United States Patent
Ojima et al.

(10) Patent No.: US 8,232,410 B2
(45) Date of Patent: Jul. 31, 2012

(54) BENZIMIDAZOLES AND PHARMACEUTICAL COMPOSITIONS THEREOF

(75) Inventors: Iwao Ojima, Port Jefferson, NY (US); Seung-yub Lee, Princeton, NJ (US)

(73) Assignee: The Research Foundation of State University of New York, Albany, NY (US)

( * ) Notice: Subject to any disclaimer, the term of this patent is extended or adjusted under 35 U.S.C. 154(b) by 302 days.

(21) Appl. No.: 12/596,347

(22) PCT Filed: Apr. 21, 2008

(86) PCT No.: PCT/US2008/005084
§ 371 (c)(1),
(2), (4) Date: Dec. 14, 2009

(87) PCT Pub. No.: WO2008/130669
PCT Pub. Date: Oct. 30, 2008

(65) Prior Publication Data
US 2010/0256203 A1     Oct. 7, 2010

Related U.S. Application Data

(60) Provisional application No. 60/912,980, filed on Apr. 20, 2007.

(51) Int. Cl.
*A61K 31/4184* (2006.01)
*C07D 235/04* (2006.01)
*C07D 235/30* (2006.01)

(52) U.S. Cl. .................. 548/304.4; 548/310.7; 514/388; 514/387

(58) Field of Classification Search .............. 548/304.4, 548/310.7
See application file for complete search history.

(56) References Cited

U.S. PATENT DOCUMENTS

| 4,873,181 | A | * | 10/1989 | Miyasaka et al. ............. 430/523 |
| 2005/0124678 | A1 | | 6/2005 | Levy et al. |
| 2006/0116412 | A1 | | 6/2006 | Ng et al. |

FOREIGN PATENT DOCUMENTS

WO    WO2007105023  A1    9/2007

OTHER PUBLICATIONS

Kym et al., CA 7:8050, 1913.*
Chemical Abstracts Registry No. 709635-32-5, indexed in the Registry file on STN CAS Online Jul. 14, 2004.*
Chemical Abstracts Registry No. 384810-14-4, indexed in the Registry file on STN CAS Online Jan. 20, 2002.*
Kym et al., "Substituted alpha-Hydroxy-and alpha-Methylbenzimidazoles," Berichte Der Deutschen Chemischen Gesellschaft, 45:3238-55 (1913). CODEN: BDCGAS; ISSN: 0365-9496.

* cited by examiner

*Primary Examiner* — Laura L. Stockton
(74) *Attorney, Agent, or Firm* — Hoffman & Baron, LLP

(57) ABSTRACT

The present invention relates to novel benzimidazole derivatives and pharmaceutically acceptable salts thereof. Another aspect of the invention relates to methods of treating a patient infected by *Mycobacterium tuberculosis* or *Francisella tulerensis* by administering to the patient a benzimidazole derivative or a pharmaceutically acceptable salt thereof.

24 Claims, No Drawings

BENZIMIDAZOLES AND PHARMACEUTICAL COMPOSITIONS THEREOF

CROSS-REFERENCE TO RELATED APPLICATION

This application is the U.S. National Phase of, and Applicants claim priority from, International Application Number PCT/US2008/005084 filed 21 Apr. 2008 and U.S. Provisional Patent Application No. 60/912,980 filed 20 Apr. 2007, each of which are incorporated herein by reference.

BACKGROUND OF THE INVENTION

Tuberculosis (TB) was one of the first infectious diseases to be identified. More than fifty years of research has been directed to controlling and eliminating this disease. However, the eradication of TB is still one of the most prominent challenges for basic and clinical research scientists.

Once thought to be under control, TB case reports in the U.S. increased sharply in the early 1990's. Although, this trend has reversed and the reported numbers of new cases has steadily declined in industrialized countries, TB remains a major global public health threat. Recent statistics from the WHO estimate that there are approximately 8.4 million new cases every year with a global mortality rate of 23% or approximately 2 million deaths per year.

Poor chemotherapeutics and inadequate local-control programs contribute to the inability to manage TB and lead to the emergence of drug resistant strains of the bacteria that cause *Mycobacterium tuberculosis* (Mtb). A survey conducted at 58 international sites between 1996 and 1999 found exceptionally high rates of single and multidrug-resistant strains in Estonia, Latvia and Russia, and revealed that countries such as China and Iran were developing a high prevalence of multidrug-resistance (MDR-TB). See Kruuner, A., Sillastu, H., Danilovitsh, M., Levina, K., Svenson, S. B., Kallenius, G., and Hoffner, S. E. (1998) *Drug resistant tuberculosis in Estonia, Int J Tuberc Lung Dis* 2, 130-3. Significantly, MDR-TB is much more difficult to treat than sensitive TB, requiring administration of more expensive, second-line antibiotics for up to two years. The frequency of resistance to at least one of the first-line TB drugs (isoniazid (INH), rifampicin (RIF), pyrazinamide or ethambutol) ranged from 1.7% in Uruguay to 36.9% in Estonia. The frequency of resistance is indicative of the global problem involving not only the spread of Mtb, but also treatment.

Finally, of critical importance is the role of TB as a major opportunistic pathogen in patients with HIV/AIDS. Consequently, there is a pressing need for the development of novel TB drugs that are effective against both sensitive and resistant Mtb strains.

Likewise, new drugs are needed to treat patients infected by *Francisella tulerensis*, the bacteria which causes tularemia. Tularemia is primarily enzootic, however, in humans, it causes lesions and flu-like symptoms. Finding new methods of treating *F. tulerensis* is of great importance because it is one of the most pathogenic microorganisms presently known. As such, it is currently listed as a category A select agent by the Centers for Disease Control and Prevention because of its potential as a bioterrorism agent.

SUMMARY OF THE INVENTION

The invention relates to a molecule having formula I:

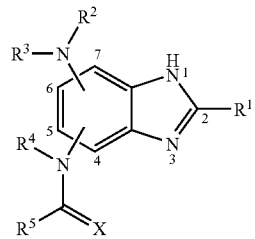

wherein:
$R^1$ represents $NH_2$, $NHR^6$, $NR^9R^{10}$, $NR^6CONR^9R^{10}$, $NR^6CSNR^9R^{10}$, OH, $OR^6$, SH, $SR^6$, CHO, $COOR^6$, $COR^6$, $CH_2OH$, $CR^7R^8OH$, $CH_2OR^6$, $CR^7R^8OR^6$, $CH_2NH_2$, $CR^7R^8NH_2$, $CR^7R^8NR^9R^{10}$, alkyl, cycloalkyl, aryl, or halo;
$R^2$ and $R^4$ independently represent H, alkyl, cycloalkyl, or aryl;
$R^3$ represents alkyl, cycloalkyl, or aryl;
$R^5$ represents H, $R^6$, $OR^6$, $SR^6$, $NH_2$, $NHR^6$, or $NR^9R^{10}$;
X represents O, S, NH, or $NR^6$;
$R^6$, $R^7$, $R^8$, $R^9$, and $R^{10}$ independently represent alkyl, cycloalkyl, aryl, or halo;
$R^2$ and $R^3$; $R^4$ and $R^5$; and $R^9$ and $R^{10}$ independently, may be combined to represent a heterocyclic alkyl or heterocyclic aryl;
$R^7$ and $R^8$ may be combined to represent a cycloalkyl;
alkyl groups are branched or unbranched, saturated or unsaturated, and have 1-18 carbon atoms in their longest chain;
cycloalkyl groups are carbocyclic or heterocyclic, fused or unfused, non-aromatic ring systems having a total of 5-16 ring members including substituent rings;
aryl groups are carbocyclic or heterocyclic;
carbocyclic aryl groups are fused or unfused ring systems having a total of 6-16 ring members including substituent rings;
heterocyclic aryl groups are fused or unfused ring systems having a total of 5-16 ring members including substituent rings;
halo substituents are fluoro, chloro, or bromo;
each alkyl, cycloalkyl, and aryl, independently, may be unsubstituted or substituted with one or more substituent at any position;
alkyl substituents are halo, hydroxyl, $OR^6$, $SR^6$, $NH_2$, $NHR^6$, $NR^9R^{10}$, cycloalkyl, or aryl;
cycloalkyl substituents are halo, hydroxyl, $OR^6$, $SR^6$, $NH_2$, $NHR^6$, $NR^9R^{10}$, alkyl, cycloalkyl, or aryl;
aryl substituents are halo, hydroxyl, $OR^6$, $SR^6$, $NH_2$, $NHR^6$, $NR^9R^{10}$, alkyl, cycloalkyl, aryl, nitro, or carboxyl; and
heterocyclic alkyl and heterocyclic aryl have at least one heteroatom selected from oxygen, nitrogen and sulfur; and
pharmaceutically acceptable salts thereof.

The invention also relates to a method of treating a patient infected with *Mycobacterium tuberculosis* or *Francisella tulerensis*, the method comprising administering to the patient the compound of formula I or a pharmaceutically acceptable salt thereof.

DETAILED DESCRIPTION

The invention relates to novel benzimidazole derivatives. These benzimidazole derivatives can be used to treat a patient infected by *Mycobacterium tuberculosis* or *Francisella tulerensis*.

The molecules have formula I:

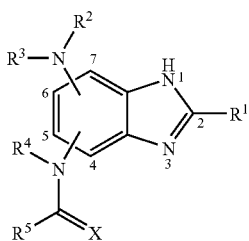

In this formula, $R^1$ represents $NH_2$, $NHR^6$, $NR^9R^{10}$, $NR^6CONR^9R^{10}$, $NR^6CSNR^9R^{10}$, OH, $OR^6$, SH, $SR^6$, CHO, $COOR^6$, $COR^6$, $CH_2OH$, $CR^7R^8OH$, $CH_2OR^6$, $CR^7R^8OR^6$, $CH_2NH_2$, $CR^7R^8NH_2$, $CR^7R^8NR^9R^{10}$, alkyl, cycloalkyl, aryl, or halo.

$R^2$ and $R^4$ independently represent H, alkyl, cycloalkyl, or aryl. For example, $R^2$ may represent ethyl and $R^4$ may represent H.

$R^3$ represents alkyl, cycloalkyl, or aryl. For example, $R^3$ may represent tetrahydrofuranyl or ethyl.

In another aspect of the invention, $R^3$ represents $COR^6$.

In a preferred embodiment, when $R^2$ represents H, $R^3$ is not methyl.

$R^5$ represents H, $R^6$, $OR^6$, $SR^6$, $NH_2$, $NHR^6$, or $NR^9R^{10}$. $R^6$, $R^7$, $R^8$, $R^9$, and $R^{10}$ independently represent alkyl, cycloalkyl, aryl, or halo. Preferably, $R^6$, $R^7$, $R^8$, $R^9$, and $R^{10}$ independently represent alkyl, cycloalkyl, or aryl. More preferably, $R^6$, $R^7$, $R^8$, $R^9$, and $R^{10}$ independently represent alkyl or aryl.

$R^2$ and $R^3$; $R^4$ and $R^5$; and $R^9$ and $R^{10}$, independently, may be combined to represent a heterocyclic alkyl or heterocyclic aryl ring. For example, $R^2$ and $R^3$ can be combined to represent a heterocyclic alkyl ring, resulting in the following structure:

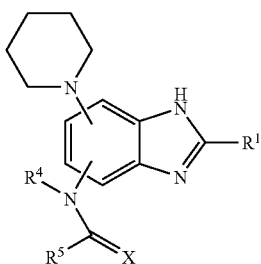

Similarly, $R^4$ and $R^5$ can be combined to represent a heterocyclic alkyl ring, resulting in the following structure:

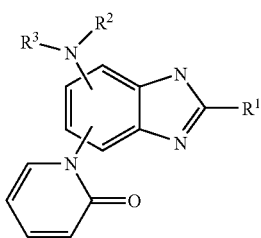

$R^7$ and $R^8$ may be combined to represent a cycloalkyl.

Alkyl groups are branched or unbranched, saturated or unsaturated, and have 1-18 carbon atoms in their longest chain. Some examples of suitable straight-chained, saturated alkyl groups include methyl, ethyl, n-propyl, n-butyl, n-pentyl, n-hexyl groups and dodecyl and hexadecyl. Preferred straight chain, saturated alkyl groups include methyl and ethyl.

Some examples of suitable branched, saturated alkyl groups include isopropyl, iso-butyl, sec-butyl, t-butyl, 1-methylbutyl, 2-methylbutyl, 3-methylbutyl (isopentyl), 1,1-dimethylpropyl, 1,2-dimethylpropyl, 2,2-dimethylpropyl (neopentyl), 1-methylpentyl, 2-methylpentyl, 3-methylpentyl, 4-methylpentyl groups, and 2-methyl, 5-ethyldecyl. Preferred branched, saturated alkyl groups include isopropyl and t-butyl.

Some examples of unsaturated alkyl groups include ethenyl, ethynyl, propenyl, propargyl, isopropenyl, crotyl, 1-hexenyl, and 1-octenyl.

Cycloalkyl groups are carbocyclic or heterocyclic, fused or unfused, non-aromatic ring systems having a total of 5-16 ring members including substituent rings. Ring systems are monocyclic, bicyclic, tricyclic, or tetracyclic and can be bridged or non-bridged.

Some examples of carbocyclic alkyl groups include cyclobutanyl, cyclopentanyl, cyclohexanyl, and cycloheptanyl. Examples of fused carbocyclic alkyl groups include indenyl, isoindenyl. Bridged groups include bicyclo[2.2.1]heptane, bicyclo[5.2.0]nonane, and bicyclo[5.2.0]nonane.

Some examples of heterocyclic alkyl groups include pyrrolidinyl, piperidinyl, piperazinyl, tetrahydrofuranyl, morpholino, and oxazolidinyl. Examples of fused heterocyclic alkyl groups include benzomorpholino, benzopyrrolidinyl, indolinyl, and benzopiperidinyl.

Aryl groups can be either carbocyclic or heterocyclic.

Carbocyclic aryl groups are fused or unfused ring systems having a total of 6-16 ring members including substituent rings. A preferred unfused carbocyclic aryl group is phenyl.

Some examples of fused carbocyclic aryl groups include naphthyl, phenanthryl, anthracenyl, triphenylenyl, chrysenyl, and pyrenyl.

Heterocyclic aryl groups are fused or unfused ring systems having a total of 5-16 ring members including substituent rings.

Some examples of unfused heterocyclic aryl groups include thiophenyl, furyl, pyrrolyl, pyrazolyl, imidazolyl, oxazolyl, thiazolyl, pyridinyl, pyridazinyl, pyrimidinyl, and pyrazinyl. Some examples of fused heterocyclic aryl groups include purinyl, 1,4-diazanaphthalenyl, indolyl, benzimidazolyl, 4,5-diazaphenanthrenyl, benzoxazolyl, isoindolyl, quinolinyl, isoquinolinyl, and benzofuranyl.

Halo substituents are fluoro, chloro, or bromo.

Each alkyl, cycloalkyl, and aryl, independently, may be unsubstituted or substituted with one or more substituent at any position. Alkyl substituents are halo, hydroxyl, $OR^6$, $SR^6$, $NH_2$, $NHR^6$, $NR^9R^{10}$, cycloalkyl, or aryl. Cycloalkyl substituents are halo, hydroxyl, $OR^6$, $SR^6$, $NH_2$, $NHR^6$, $NR^9R^{10}$, alkyl, cycloalkyl, or aryl. Aryl substituents are halo, hydroxyl, $OR^6$, $SR^6$, $NH_2$, $NHR^6$, $NR^9R^{10}$, alkyl, cycloalkyl, aryl, nitro, or carboxyl.

Heterocyclic alkyl and heterocyclic aryl have at least one heteroatom selected from oxygen, nitrogen, and sulfur.

X represents O, S, NH, or $NR^6$. $R^6$ is described above.

In the present invention, various parameters are defined (e.g. $R^1$, $R^2$, $R^3$, $R^4$, X). Within each parameter, more than one element (e.g. chemical moieties) are listed. It is to be understood that the instant invention contemplates embodiments in which each element listed under one parameter may be combined with each and every element listed under any other parameter. For example, X is identified above as representing O, S, NH, or $NR^6$. $R^5$ is identified above as being H, $R^6$, $OR^6$, $SR^6$, $NH_2$, $NHR^6$, or $NR^9R^{10}$. Each element of X (O, S, NH or $NR^6$) can be combined with each and every element of $R^5$ (H, $R^6$, $OR^6$, $SR^6$, $NH_2$, $NHR^6$, or $NR^9R^{10}$). For example, in one embodiment, X may be O and $R^5$ may be H. Alternatively, X may be NH and $R^5$ may be $NR^9R^{10}$, etc. Similarly, a third parameter is $R^4$, in which the elements are defined as H, alkyl, cycloalkyl, or aryl. Each of the above embodiments may be combined with each and every element of $R^4$. For example, in the embodiment wherein X is O and $R^5$ is H, $R^4$ may be H (or any other chemical moiety within the element of $R^4$).

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Pharmaceutically Acceptable Salts

The present invention also relates to pharmaceutically acceptable salts of the benzimidazole derivatives. The pharmaceutically acceptable salts include the conventional non-toxic salts of the benzimidazole derivatives as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the benzimidazole derivatives of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Synthesis of the Benzimidazole Derivatives

The benzimidazoles of the present invention can be synthesized by methods known in the art. The following scheme represents one approach to the synthesis of the compounds of the invention.

Scheme I shows an example of a synthesis that yields individual compounds of the invention or a library of compounds of the invention. For example, the compounds of the invention may be made using polymer-assisted solution-phase (PASP) synthesis. PASP is a parallel synthesis method for creation of a trisubstituted benzimidazoles (BAZ-1) library using 2,4-dinitro-5-fluoroaniline (1) as the starting material.

Scheme 1

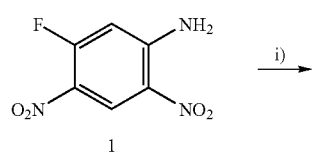

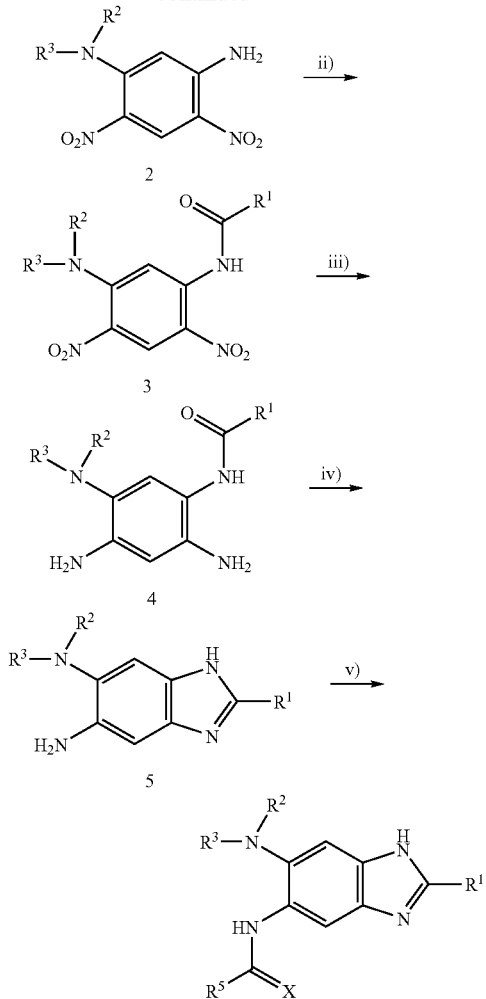

i) $R^2R^3NH$, DIPEA; ii) Acid chloride, pyridine; iii) Pd-C/HCOONH$_4$; iv) 6N HCl/dioxne-MeOH; v) (RCO)$_2$O, RSO$_2$Cl, RCOCl, or RCON, NH$_2$-Scavenger The first step involves the nucleophilic substitution of compound 1 with a secondary amine in the presence of N,N-diisopropylethylamine. The reaction produces compound 2 in high yields and purity at room temperature.

Then the acylation of the free amino group of compound 2 with an acyl or aroyl chloride takes place. This reaction occurs under reflux conditions using pyridine as the solvent.

Subsequently, reduction of the aromatic m-dinitro groups of compound 3 using HCOO$^-$NH$_4^+$ and Pd—C generates diamine compound 4. The benzimidazole ring is formed through acid-catalyzed dehydration.

The free aromatic amino group of compound 5 is modified in different ways. To introduce diversity at the —C(X)—$R^5$ position, anhydride, acyl chloride, sulfonyl chloride, and isocyanate are used as modifying agents. The modification of the aromatic amine moiety takes place smoothly in dry dichloromethane and all excess acylating reagents are scavenged by commercially available aminomethylated polystyrene resin (from nova-biochem) to give the desired product 6 in 80-95% yield.

Uses of the Benzimidazole Derivatives

The invention also relates to a method of treating a patient infected with *Mycobacterium tuberculosis* or *Francisella tul-*

*erensis*. The method comprises administering to the patient the compound of formula (I) or a pharmaceutically acceptable salt thereof.

The method and compounds of the invention may be employed alone, or in combination with other anti-bacterial agents. Other anti-bacterial agents include isoniazid, rifampin, pyrazinamide, rifabutin, streptomycin and ciprofloxacin. The combination of these anti-bacterial agents and the compounds of the invention will provide new agents for the treatment of tuberculosis, including MDR-TB and XDR-TB, and tularemia.

An effective amount of a compound of formula (I) or a pharmaceutically acceptable salt thereof as used herein is any amount effective to treat a patient infected by Mtb or *F. tulerensis*. Modes of administration and doses can be determined by those having skill in the art. An effective amount of the compound will vary with the group of patients (age, sex, weight, etc.), the nature and severity of the condition to be treated, the particular compound administered, and its route of administration. Amounts suitable for administration to humans are routinely determined by physicians and clinicians during clinical trials.

The minimum dose of the compound is the lowest dose at which efficacy is observed. For example, the minimum dose of the compound may be about 0.1 mg/kg/day, about 1 mg/kg/day, or about 3 mg/kg/day.

The maximum dose of the compound is the highest dose at which efficacy is observed in a patient, and side effects are tolerable. For example, the maximum dose of the compound may be about 10 mg/kg/day, about 9 mg/kg/day, or about 8 mg/kg/day.

A benzimidazole derivative useful in the methods of the present invention may be administered by any method known in the art. Some examples of suitable modes of administration include oral and systemic administration. Systemic administration can be enteral or parenteral. Liquid or solid (e.g., tablets, gelatin capsules) formulations can be employed.

Parenteral administration of the benzimidazole derivative include, for example intravenous, intramuscular, and subcutaneous injections. For instance, a chemical compound may be administered to a patient by sustained release, as is known in the art. Sustained release administration is a method of drug delivery to achieve a certain level of the drug over a particular period of time.

Other routes of administration include oral, topical, intrabronchial, or intranasal administration. For oral administration, liquid or solid formulations may be used. Some examples of formulations suitable for oral administration include tablets, gelatin capsules, pills, troches, elixirs, suspensions, syrups, and wafers. Intrabronchial administration can include an inhaler spray. For intranasal administration, administration of a chemical compound can be accomplished by a nebulizer or liquid mist.

The chemical compound can be formulated in a suitable pharmaceutical carrier. In this specification, a pharmaceutical carrier is considered to be synonymous with a vehicle or an excipient as is understood by practitioners in the art. Examples of carriers include starch, milk, sugar, certain types of clay, gelatin, stearic acid or salts thereof, magnesium or calcium stearate, talc, vegetable fats or oils, gums and glycols.

The chemical compound can be formulated into a composition containing one or more of the following: a stabilizer, a surfactant, preferably a nonionic surfactant, and optionally a salt and/or a buffering agent.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the chemical compound.

The surfactant is preferably a nonionic surfactant, such as a polysorbate. Some examples of suitable surfactants include Tween 20, Tween 80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example sodium chloride, or sodium/potassium phosphate, respectively. Preferably, the buffering agent maintains the pH of the chemical compound formulation in the range of about 5.5 to about 7.5. The salt and/or buffering agent is also useful to maintain the osmolality at a level suitable for administration to a patient. Preferably the salt or buffering agent is present at a roughly isotonic concentration of about 150 mM to about 300 mM.

The chemical compound can be formulated into a composition which may additionally contain one or more conventional additives. Some examples of such additives include a solubilizer such as, for example, glycerol; an antioxidant such as for example, benzalkonium chloride (a mixture of quaternary ammonium compounds, known as "quart"), benzyl alcohol, chloretone or chlorobutanol; anaesthetic agent such as, for example a morphine derivative; or an isotonic agent etc. As a further precaution against oxidation or other spoilage, the composition may be stored under nitrogen gas in vials sealed with impermeable stoppers.

EXAMPLES

Examples have been set forth below for the purposes of illustration and to describe the best mode of the invention at the present time. The scope of the invention is not to be in any way limited by the examples set forth herein.

Example 1

Synthesis of 6-diethylamino-5-(4-methoxybenzoyl)amino-2-(2-methoxyphenyl)-1H-benzo[d]imidazole, a key intermediate for the synthesis of a library of compounds (the process includes three steps)

(a) Synthesis of 1-amino-3-diethylamino-4,6-dinitrobenzene

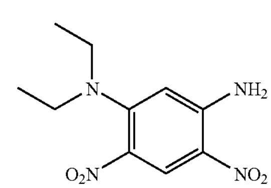

To a solution of 2,4-dinitro-5-fluoroaniline (1.6 g, 8.0 mmol) in 20 mL of THF, a mixture of DIPEA (1.1 g, 8.8 mmol) and diethylamine (644 mg, 8.8 mmol) in 5 mL of THF was added slowly. The reaction mixture was stirred at room temperature for 1 h. Water (100 mL) was added to give the desired product as a yellow precipitate. The product was collected by filtration and washed with water (200 mL). The filtrate was concentrated to dryness in vacuo to give the desired product (1.8 g, 90% yield) as a bright yellow solid: $^1$H-NMR (300 MHz, CDCl$_3$) δ 1.96 (t, 6H, J=7.2 Hz), 3.24 (q, 4H, J=7.2 Hz), 6.08 (s, 1H), 8.75 (s, 1H); $^{13}$C NMR (75 MHz, CDCl$_3$) δ 12.1, 45.7, 102.7, 123.3, 128.2, 131.6, 147.8, 149.4; ESI MS m/z 255.1 [M+H]$^+$.

(b) Synthesis of 5-(diethylamino)-2,4-dinitro-1-(2-methoxybenzoyl)aminobenzene

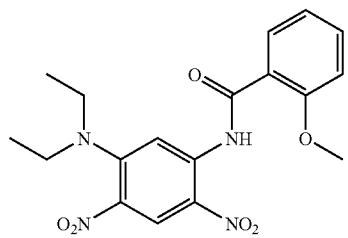

To a solution of 1-amino-3-diethylamino-4,6-dinitrobenzene (508 mg, 2.0 mmol) in 5 mL of pyridine, 2-methoxybenzoyl chloride (680 mg, 4.0 mmol) was added. After refluxing for 5 h, 50 mL of water was added to the reaction mixture, and the precipitate was collected by filtration and washed with 200 mL of water. Recrystallization from dichloromethane and methanol gave the desired product (622 mg, 80% yield) as a yellow solid: $^1$H-NMR (300 MHz, CDCl$_3$) δ 1.29 (t, 6H, J=7.2 Hz), 3.39 (q, 4H, J=7.2 Hz), 4.13 (s, 3H), 7.07 (d, 1H, J=8.1), 7.11 (t, 1H, J=9.8 Hz), 7.55 (t, 1H, J=7.8 Hz), 8.23 (d, 1H, J=8.1 Hz), 8.83 (s, 1H), 8.98 (s, 1H); ESI MS m/z 389.1 [M+H]$^+$.

(c) Synthesis of 5-amino-6-diethylamino-2-(2-methoxyphenyl)-1H-benzo[d]-imidazole

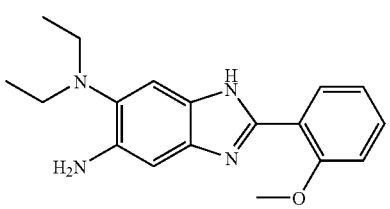

To the solution of 5-(diethylamino)-2,4-dinitro-1-(2-methoxybenzoyl)aminobenzene (388 mg, 1.0 mmol) in 10 mL of 1,4-dioxane and 10 mL of methanol, was added ammonium formate (1.5 g) and 10% Pd/C (200 mg) under nitrogen atmosphere. The reaction mixture was stirred for 30 min. The Pd/C and excess ammonium formate were filtered. Conc. HCl (10 mL) was added to the filtrate. After heating at 75° C. for 18 h, the reaction mixture was basified to pH 8 with saturated K$_2$CO$_3$ solution. The reaction mixture was diluted with 200 mL of ethyl acetate, washed with brine, and dried over anhydrous MgSO$_4$. The reaction mixture was filtered and concentrated in vacuo to afford the crude product (280 mg, 90% yield). The crude product was then purified by column chromatography on silica gel using EtOAc as the eluant to afford the desired product (188 mg, 61% yield) as a brown solid: $^1$H-NMR (300 MHz, CDCl$_3$) δ 1.01 (t, 6H, J=7.2 Hz), 3.01 (q, 4H, J=7.2 Hz), 4.05 (s, 3H), 6.92 (s, 1H), 7.03 (d, 1H, J=8.1 Hz), 7.11 (t, 1H, J=8.1 Hz), 7.36 (t, 1H, J=6.9), 7.41 (s, 1H), 8.52 (d, 1H, J=7.8 Hz); ESI MS m/z 311.2 [M+H]$^+$.

Examples 2-7

The following key intermediates were prepared and characterized in the same manner as Example 1.

5-Amino-6-diethylamino-2-(cyclohexyl)-1H-benzo[d]-imidazole

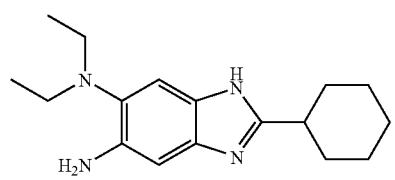

Brown solid; $^1$H-NMR (300 MHz, CDCl$_3$) δ 0.95 (t, 6H, J=7.2 Hz), 1.2-2.2 (m, 10H), 2.82 (m, 1H), 2.92 (q, 4H, J=7.2 Hz), 6.90 (s, 1H), 7.33 (s, 1H); ESI MS m/z 287.1 [M+H]$^+$.

5-Amino-6-diethylamino-2-(4-fluorophenyl)-1H-benzo[d]-imidazole

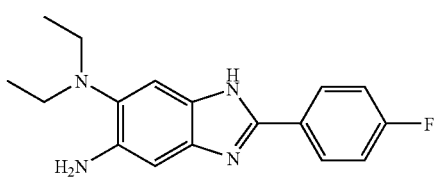

Brown solid; $^1$H-NMR (300 MHz, CDCl$_3$) δ 0.94 (t, 6H, J=7.2 Hz), 2.91 (q, 4H, J=7.2 Hz), 6.80 (s, 1H), 7.02 (t, 2H, J=8.7 Hz), 7.27 (s, 1H), 7.98 (ddd, 2H, J=1.8, 5.4, 8.7 Hz); ESI MS m/z 299.1 [M+H]$^+$.

5-Amino-6-diethylamino-2-(phenyl)-1H-benzo[d]-imidazole

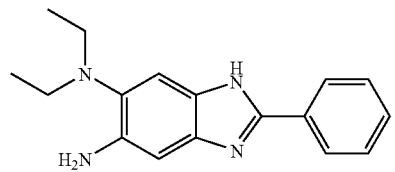

Brown solid; $^1$H-NMR (300 MHz, CDCl$_3$) δ 0.92 (t, 6H, J=7.2 Hz), 2.92 (q, 4H, J=7.2 Hz), 6.85 (s, 1H), 7.32 (s, 1H), 7.41 (m, 3H), 8.01 (dd, 2H, J=1.8, 8.4 Hz); ESI MS m/z 281.1 [M+H]$^+$.

5-Amino-6-diethylamino-2-(4-methylphenyl)-1H-benzo[d]-imidazole

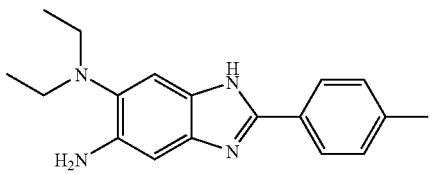

Brown solid; ¹H-NMR (300 MHz, CDCl₃) δ 0.91 (t, 6H, J=7.2 Hz), 2.90 (q, 4H, J=7.2 Hz), 2.33 (s, 3H), 6.79 (s, 1H), 7.13 (d, 2H, J=7.8 Hz), 7.32 (s, 1H), 7.99 (d, 2H, J=7.8 Hz); ESI MS m/z 295.1 [M+H]⁺.

5-Amino-6-diethylamino-2-(4-methoxyphenyl)-1H-benzo[d]-imidazole

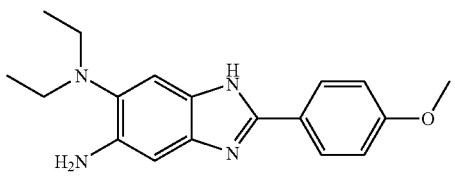

Brown solid; ¹H-NMR (300 MHz, CDCl₃) δ 0.93 (t, 6H, J=7.2 Hz), 2.92 (q, 4H, J=7.2 Hz), 4.03 (s, 3H), 6.73 (s, 1H), 6.75 (d, 2H, J=8.4 Hz), 7.10 (d, 2H, J=8.4 Hz) 7.16 (s, 1H); ESI MS m/z 311.1 [M+H]⁺.

5-Amino-6-diethylamino-2-(1-naphthyl)-1H-benzo[d]-imidazole

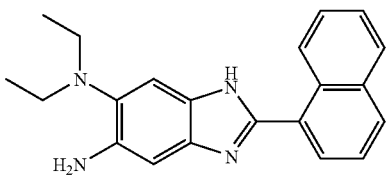

Brown solid; ¹H-NMR (300 MHz, CDCl₃) δ 0.91 (t, 6H, J=7.2 Hz), 2.92 (q, 4H, J=7.2 Hz), 6.65 (s, 1H), 7.10 (s, 1H), 7.35 (t, 1H, J=7.5 Hz), 7.44 (t, 2H, J=4.2 Hz), 7.67 (d, 1H, J=6.3), 7.83 (m, 2H), 8.64 (m, 1H); ESI MS m/z 349.2 [M+H]⁺.

Example 8

Synthesis of 6-diethylamino-5-(4-methoxybenzoyl)amino-2-(2-methoxyphenyl)-1H-benzo[d]imidazole

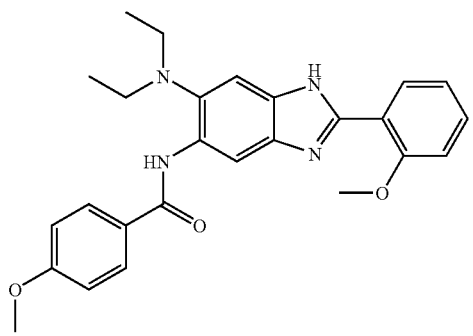

To a solution of 5-amino-6-diethylamino-2-(2-methoxyphenyl)-1H-benzo[d]-imidazol (200 mg, 0.64 mmol) in dichloromethane (5 mL), 2-methoxybenzoyl chloride (112 mg, 0.64 mmol) was added and stirred at room temperature for 3 h. The reaction mixture was concentrated in vacuo and then purified by column chromatography on silica gel using hexane/EtOAc (4/1) as the eluant to afford the desired product (210 mg, 78%) as a white powder: ¹H-NMR (300 MHz, CDCl₃) δ 1.00 (t, 6H, J=7.2 Hz), 3.05 (q, 4H, J=7.2 Hz), 3.86 (s, 3H), 4.04 (s, 3H), 6.85 (d, 2H, J=9 Hz), 7.03 (d, 1H, J=8.7 Hz), 7.13 (t, 1H, J=7.2 Hz), 7.39 (t, 1H, J=7.2 Hz), 7.66 (s, 1H), 7.91 (d, 2H, J=9 Hz), 8.88 (s, 1H); ¹³C NMR (75 MHz, CDCl₃) δ12.9, 50.4, 55.3, 55.7, 111.4, 113.8, 117.9, 121.5, 127.8, 128.6, 129.6, 130.8, 132.8, 135.8, 149.9, 156.6, 162.1, 164.1; ESI MS m/z 445.4 [M+H]⁺.

Example 9

Synthesis of 6-diethylamino-5-(4-chlorobenzoyl)amino-2-(2-methoxyphenyl)-1H-benzo[d]imidazole

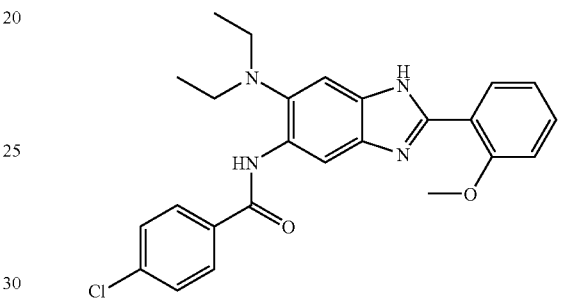

5-Amino-6-diethylamino-2-(2-methoxyphenyl)-1H-benzo[d]-imidazole (187 mg, 0.6 mmol) was reacted with 4-chlorobenzoyl chloride (105 mg, 0.6 mmol) in the same manner as that described above to give the desired product (216 mg, 80% yield) as pale yellow powder: ¹H-NMR (300 MHz, CDCl₃) δ 0.99 (t, 6H, J=7.2 Hz), 3.05 (q, 4H, J=7.2 Hz), 4.07 (s, 3H), 7.05 (d, 1H, J=8.4 Hz), 7.11 (t, 1H, J=7.8 Hz), 7.41 (t, 1H, J=7.8 Hz), 7.47 (d, 2H, J=8.4 Hz), 7.67 (s, 1H), 7.88 (d, 2H, J=8.4 Hz), 8.55 (d, 1H, J=6.9 Hz), 8.86 (s, 1H); ¹³C NMR (75 MHz, CDCl₃) δ13.1, 50.6, 55.9, 111.5, 117.7, 121.7, 128.3, 129.0, 129.8, 131.1, 132.5, 133.9, 136.0, 137.7, 150.2, 156.7, 163.4; ESI MS m/z 449.2 [M+H]⁺.

Example 10

Synthesis of 6-diethylamino-5-(benzoyl)amino-2-(cyclohexyl)-1H-benzo[d]-imidazole

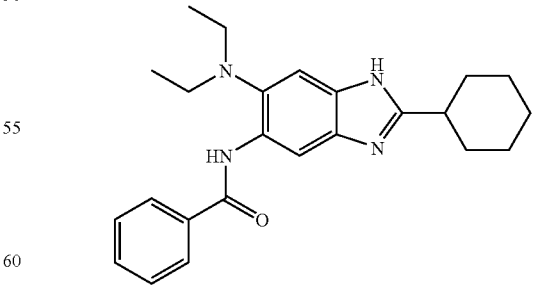

5-Amino-6-diethylamino-2-(cyclohexyl)-1H-benzo[d]-imidazole (27 mg, 0.1 mmol) was reacted with benzoyl chloride (11 mg, 0.1 mmol) in the same manner as that described above to give the desired product (27 mg, 74% yield) as white powder: ¹H-NMR (300 MHz, CDCl₃) δ 0.98 (t, 6H, J=7.2

Hz), 1.16 (m, 3H), 1.57-1.70 (m, 5H), 1.98 (m, 2H), 2.87 (m, 1H), 3.03 (q, 4H, J=7.2 Hz), 7.57 (m, 3H), 7.57 (s, 1H), 8.00 (dd, 2H, J=1.8, 8.4 Hz), 8.96 (s, 1H); ESI MS m/z 391.0 [M+H]⁺.

Example 11

Synthesis of 6-diethylamino-5-(4-methoxybenzoyl) amino-2-(cyclohexyl)-1H-benzo[d]imidazole

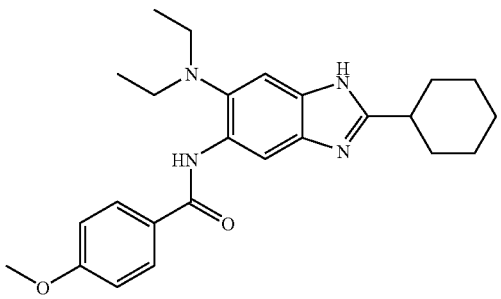

5-Amino-6-diethylamino-2-(cyclohexyl)-1H-benzo[d]-imidazole (28 mg, 0.1 mmol) was reacted with 4-methoxy-benzoyl chloride (17 mg, 0.1 mmol) in the same manner as that described above to give the desired product (33 mg, 79% yield) as white powder: ¹H-NMR (300 MHz, CDCl₃) δ 0.97 (t, 6H, J=7.2 Hz), 1.16 (m, 3H), 1.57-1.70 (m, 5H), 1.98 (m, 2H), 2.87 (m, 1H), 3.01 (q, 4H, J=7.2 Hz), 7.05 (d, 2H, J=8.7 Hz), 7.57 (s, 1H), 7.96 (d, 2H, J=8.7 Hz), 8.94 (s, 1H); ESI MS m/z 421.0 [M+H]⁺.

Example 12

Synthesis of 7-amino-5-(methoxycarbonyl)amino-2-(4-bromophenyl)-1H-benzo[d]-imidazole (the process includes three steps)

(a) Synthesis of 4-amino-3,5-dinitro-1-(methoxycarbonyl)aminobenzene

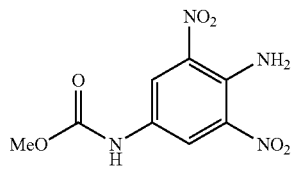

A suspension of 4-amino-3,5-dinitrobenzamide (543 mg, 2.4 mmol) in 4M HCl (20 mL) was refluxed overnight. The reaction mixture was cooled and the precipitated solid was filtered to give 4-amino-3,5-dinitrobenzoic acid as yellow solid: ¹H-NMR (300 MHz, DMSO-d₆) δ 8.80 (s, 2H). 4-Amino-3,5-dinitrobenzoic acid, thus obtained, was dissolved in SOCl₂ (4 mL) and refluxed overnight. The reaction mixture was cooled down to room temperature and concentrated under reduced pressure to remove excess SOCl₂. The crude product was immediately dissolved in acetone (2.4 mL) in an ice-bath. To this solution was added dropwise NaN₃ (0.29 g, 3.84 mmol) in ice-water (0.88 mL). The mixture was stirred for 20 min at 0° C. until a solid precipitated out. After dilution with ice-water (12 mL), the reaction mixture was extracted with CH₂Cl₂ (6 mL×2), dried over MgSO₄ at 0° C. for 1 h, and filtered. The filtrate was concentrated on a rotary evaporator (below room temperature), and the residue dissolved in toluene (15 mL). After refluxing for 2 h, the reaction mixture was cooled down to room temperature, and MeOH (10 mL) was added. After stirring overnight at room temperature, the reaction mixture was concentrated in vacuo and purified by flash chromatography on silica gel (hexane/EtOAc=1/1) to afford 4-amino-3,5-dinitro-1-(methoxycarbonyl)aminobenzene as bright red solid (292 mg, 45% yield): ¹H-NMR (300 MHz, CDCl₃) δ 3.73 (s, 3H), 6.60 (s, 1H), 8.30 (s, 2H), 8.64 (s, 2H); ESI MS m/z 256.9 [M+H]⁺.

(b) Synthesis of 7-amino-5-(methoxycarbonyl)amino-2-(4-bromophenyl)-1H-benzo[d]imidazole

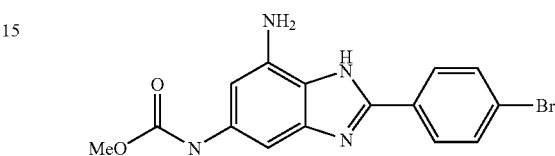

To a suspension of 4-amino-3,5-dinitro-1-(methoxycarbonyl)aminobenzene (311 mg, 1.2 mmol) in ethanol (24 mL), was added ammonium formate (1.8 g) and 10% Pd/C (120 mg) under nitrogen. The mixture was stirred at room temperature overnight. The Pd/C and excess ammonium formate were filtered off. The filtrate was treated with the sodium bisulfite adduct of 4-bromobenzaldehyde (715 mg, 0.84 mmol) at 0° C. After the solution was stirred for 12-16 h at room temperature under nitrogen, a trace of insoluble material was removed by filtration and the filtrate was concentrated on a rotary evaporator until approximately 60-70% of the solvent was removed. To the residue an equal volume of ethyl acetate was added, and the mixture was transferred to a separatory funnel. The organic layer was separated, and the water layer was extracted with ethyl acetate. The combined organic layers were washed with brine, dried over anhydrous sodium sulfate, and concentrated in vacuo to give the desired product (610 mg, 48% yield) as brown powder: ¹H-NMR (300 MHz, CD₃OD) δ 3.73 (s, 3H), 6.53 (s, 1H), 7.16 (s, 1H), 7.64 (dd, 2H, J=6.6, 1.8 Hz), 7.88 (dd, 2H, J=6.6, 1.8 Hz); ESI MS m/z 361.0 [M+H]⁺.

(c) Synthesis of 7-acetylamino-5-(methoxycarbonyl)amino-2-(4-bromophenyl)-1H-benzo[d]imidazole

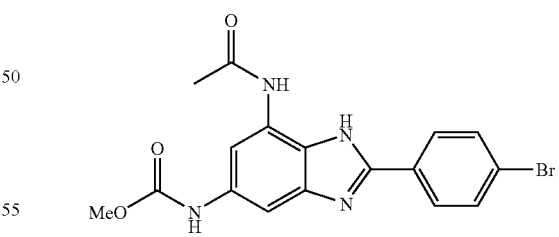

To a solution of 7-amino-5-(methoxycarbonyl)amino-2-(4-bromophenyl)-1H-benzo[d]-imidazole (60 mg, 0.17 mmol) in dichloromethane (5 mL) was added acetic anhydride (18 mg, 0.17 mmol) and the solution was stirred at room temperature for 3 h. The reaction mixture was concentrated in vacuo and purified by column chromatography on silica gel using hexane/EtOAc (4/1) as the eluant to afford the desired product (55 mg, 80%) as a pale yellow powder: ¹H-NMR (300 MHz, CD₃OD) δ 2.24 (s, 3H), 3.74 (s, 3H), 7.65 (m, 3H), 7.67 (bs, 1H), 7.90 (m, 2H); ESI MS m/z 403.0 [M+H]⁺.

Example 13

Procedure for the determination of the minimum inhibitory concentration (MIC): MIC values were determined using the microplate dilution method, previously reported [R. A. Slayden and C. E. Barry, III. "The role of KasA and KasB in the biosynthesis of meromycolic acids and isoniazid resistance in *Mycobacterium tuberculosis*", *Tuberculosis* (Edinb) 82:149-60 (2002)].

Bacteria were cultivated in liquid medium to an optical density of ~0.4 at 600 nm. The bacterial cultures were then prepared for testing by diluting 1:100 in liquid medium. A total of 50 μL of each culture was added to each well of a 96-well optical plate. Analogs were prepared at 60 μM in 100% DMSO. Compound stock solutions were diluted 1:2 in liquid medium and then distributed in the plate as 2-fold serial dilutions to achieve a concentration range of 200-0.2 mg/mL in a total final volume of 100 μL. The plates were incubated at 37° C. and evaluated for the presence of bacterial growth or non-growth by optical density using an inverted plate reading method. The $MIC_{99}$ was determined to be the lowest concentration of compound that inhibited bacterial growth. Reported MIC values represent measurements performed independently in triplicate.

A list of active compounds is included in the Appendix section.

Examples 14-16

The following key intermediates were prepared and characterized in the same manner as Example 1(a).

1-Amino-2,4-dinitro-5-morpholinobenzene

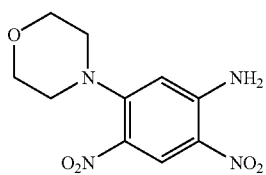

Yield 92%; $^1$HNMR (400 MHz, CDCl$_3$) δ 8.92 (s, 1H) 6.12 (s, 1H), 3.86 (t, 4H, J=6.2 Hz), 3.12 (t, 4H, J=6.2 Hz); ESI MS m/z 269.2 [M+H]$^+$.

1-Amino-2,4-dinitro-5-piperidinobenzene

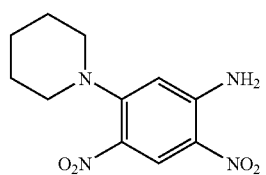

Yield 94%; $^1$HNMR (300 MHz, CDCl$_3$) δ 8.84 (s, 1H) 6.43 (bs, 2H), 3.09 (t, 4H, J=5 Hz), 1.71 (m, 4H); ESI MS m/z 267.2 [M+H]$^+$.

1-Amino-2,4-dinitro-5-(4-tert-butoxycarbonylpiperazino)benzene

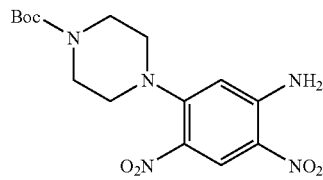

Yield 94% $^1$HNMR (400 MHz, CDCl$_3$) δ 8.91 (s, 1H) 6.16 (s, 1H), 3.61 (t, 4H, J=5 Hz), 3.09 (t, 4H, J=4.8 Hz), 1.47 (s, 9H); ESI MS m/z 368.3 [M+H]$^+$.

Examples 17-29

The following key intermediates were prepared and characterized in the same manner as Example 1(b).

1-Cyclohexanecarbonylamino-5-diethylamino-2,4-dinitrobenzene

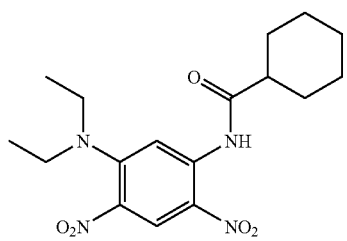

Yield 88%; $^1$HNMR (300 MHz, CDCl$_3$) δ 8.76 (s, 1H), 8.65 (s, 1H), 3.36 (q, 4H, J=10.8 Hz), 2.38-1.30 (m, 11H), 1.26 (t, 6H, J=7.2 Hz); ESI MS m/z 365.4 [M+H]$^+$.

1-(4-Methylbenzoyl)amino-5-diethylamino-2,4-dinitrobenzene

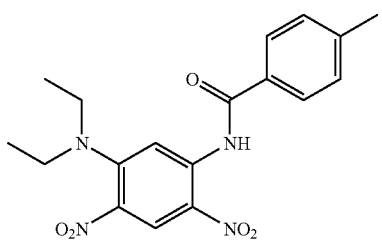

Yield 67%; $^1$HNMR (300 MHz, CDCl$_3$) δ 8.8 (d, 2H, J=5.8 Hz), 7.87 (d, 2H, J=4 Hz), 7.33 (d, 2H, J=4 Hz), 3.4 (q, 4H, J=10.6 Hz), 2.43 (s, 3H), 1.29 (t, 6H, J=7.2 Hz); ESI MS m/z 373.3 [M+H]⁺.

1-(4-Methoxybenzoyl)amino-5-diethylamino-2,4-dinitrobenzene

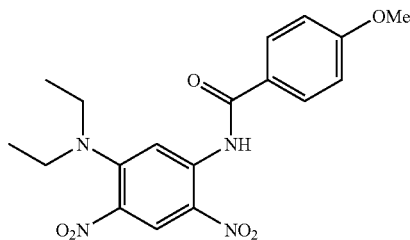

Yield 85%; ¹HNMR (300 MHz, CDCl₃) δ 11.79 (s, 1H), 8.82 (d, 2H, J=2.1 Hz), 7.96 (d, 2H, J=4.5 Hz), 7.03 (d, 2H, J=4.3 Hz), 3.39 (s, 3H), 3.41 (q, 4H, J=10.6 Hz), 1.30 (t, 6H, J=6.9 Hz); ESI MS m/z 389.3 [M+H]⁺.

1-(4-tert-Butylbenzoyl)amino-5-diethylamino-2,4-dinitrobenzene

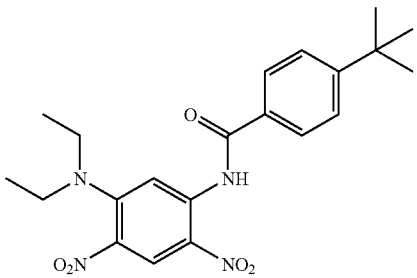

Yield 78%; ¹HNMR (300 MHz, CDCl₃) δ 8.84 (s, 1H), 8.82 (s, 1H), 7.94 (d, 2H, J=4.3 Hz), 7.56 (d, 2H, J=4.2 Hz), 3.41 (q, 4H, J=10.6 Hz), 1.37 (s, 9H), 1.30 (t, 6H, J=7.2 Hz); ESI MS m/z 415.4 [M+H]⁺.

1-(4-Fluorobenzoyl)amino-5-diethylamino-2,4-dinitrobenzene

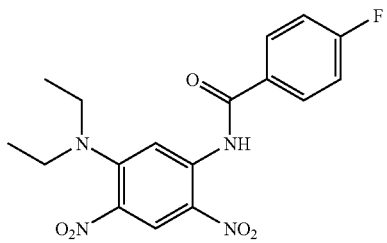

Yield 79%; ¹HNMR (300 MHz, CDCl₃) δ 11.84 (s, 1H), 8.81 (s, 1H), 8.8 (s, 1H), 8.02 (d, 2H, J=7.2 Hz), 7.22 (d, 2H, J=5.2 Hz), 3.41 (q, 4H, J=10.6 Hz), 1.30 (t, 6H, J=7.2 Hz); ESI MS m/z 377.3 [M+H]⁺.

1-Benzoylamino-5-diethylamino-2,4-dinitrobenzene

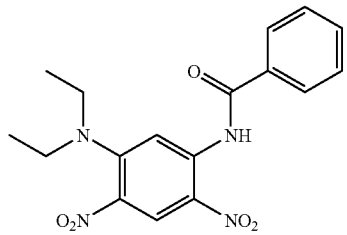

Yield 80%; ¹HNMR (300 MHz, CDCl₃) δ 11.87 (s, 1H), 8.84 (s, 1H), 8.82 (s, 1H), 8.0 (d, 2H, J=4.8 Hz), 7.63-7.55 (m, 3H), 3.41 (q, 4H, J=10.6 Hz), 1.31 (t, 6H, J=7.2 Hz); ESI MS m/z 359.3 [M+H]⁺.

1-Cyclohexanecarbonylamino-5-morpholino-2,4-dinitrobenzene

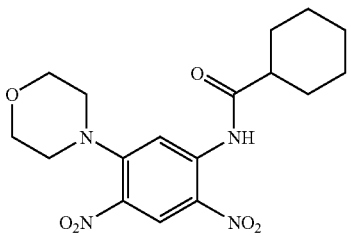

Yield 90%; ¹HNMR (400 MHz, CDCl₃) δ 10.92 (s, 1H), 8.87 (s, 1H), 8.64 (s, 1H), 3.83 (t, 4H, J=4.8 Hz), 3.28 (t, 4H, J=4.6 Hz), 2.38 (m, 1H), 2.03-1.26 (m, 11H); ESI MS m/z 379.3 [M+H]⁺.

1-(4-Methylbenzoyl-5-morpholino-2,4-dinitrobenzene

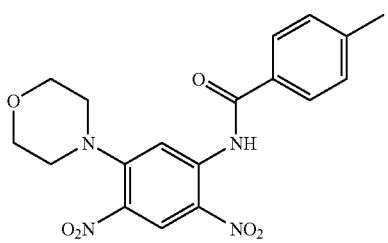

Yield 87%; ¹HNMR (400 MHz, CDCl₃) δ 11.80 (s, 1H), 8.95 (s, 1H), 8.83 (s, 1H), 7.88 (d, 2H, J=4.2 Hz), 7.36 (d, 2H, J=4 Hz), 3.88 (t, 4H, J=4.6 Hz), 3.34 (t, 4H, J=4.6 Hz), 2.46 (s, 3H); ESI MS m/z 387.3 [M+H]⁺.

1-(4-tert-Butylbenzoyl)amino-5-morpholino-2,4-dinitrobenzene

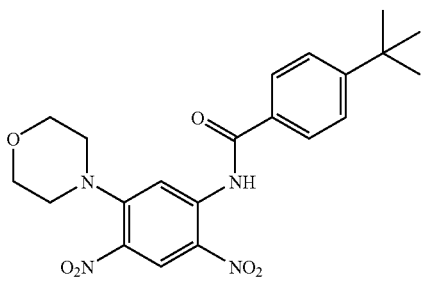

Yield 75%; ¹HNMR (400 MHz, CDCl₃) δ 11.81 (s, 1H), 8.95 (s, 1H), 8.84 (s, 1H), 7.92 (d, 2H, J=4.2 Hz), 7.57 (d, 2H, J=4.2 Hz), 3.88 (t, 4H, J=4.6 Hz), 3.34 (t, 4H, J=4.6 Hz), 1.37 (s, 9H); ESI MS m/z 429.4 [M+H]⁺.

1-Cyclohexanecarbonylamino-2,4-dinitro-5-(4-tert-butoxycarbonylpiperazin-1-yl)benzene

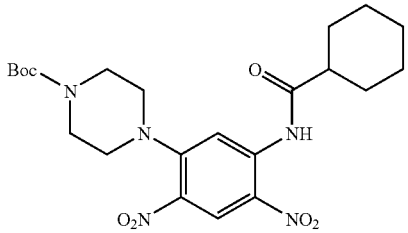

Yield 70%; ¹HNMR (400 MHz, CDCl₃) δ 10.92 (s, 1H), 8.90 (s, 1H), 8.67 (s, 1H), 3.62 (t, 4H, J=5.2 Hz), 3.28 (t, 4H, J=5.2 Hz), 2.38 (m, 1H), 2.03-1.26 (m, 11H); ESI MS m/z 478.5 [M+H]⁺.

1-Cyclohexanecarbonylamino-2,4-dinitro-5-(piperidin-1-yl)benzene

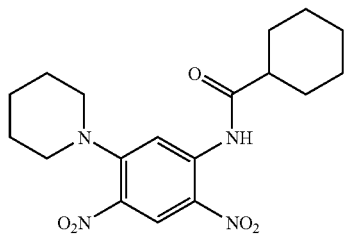

Yield 80%; ¹HNMR (300 MHz, CDCl₃) δ 10.95 (s, 1H), 8.85 (s, 1H), 8.63 (s, 1H), 3.27 (t, 4H, J=4.9 Hz), 2.38 (m, 1H), 2.03-1.26 (m, 16H); ESI MS m/z 377.4 [M+H]⁺.

1-(4-Methoxybenzoyl)amino-2,4-dinitro-5-(piperidin-1-yl)benzene

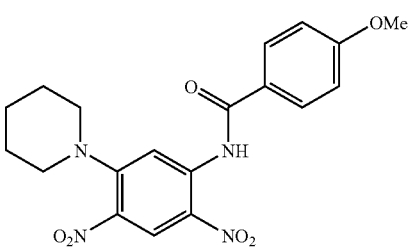

Yield 85%; ¹HNMR (300 MHz, CDCl₃) δ 11.69 (s, 1H), 8.90 (s, 1H), 8.79 (s, 1H), 7.95 (d, 2H, J=4.5 Hz), 7.03 (d, 2H, J=4.3 Hz), 3.90 (s, 3H), 3.32 (t, 4H, J=4.95 Hz), 1.75 (m, 6H); ESI MS m/z 401.3 [M+H]⁺.

1-Benzoylamino-2,4-dinitro-5-(piperidin-1-yl)benzene

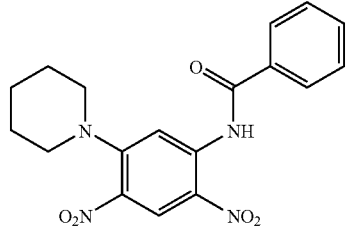

Yield 83%; ¹HNMR (300 MHz, CDCl₃) δ 11.87 (s, 1H), 8.91 (s, 1H), 8.80 (s, 1H), 7.98 (d, 2H, J=4.8 Hz), 7.66-7.55 (m, 3H), 3.33 (t, 4H, J=4.9 Hz), 1.76 (m, 6H); ESI MS m/z 371.3 [M+H]⁺.

Examples 30-34

The following key intermediates were prepared and characterized in the same manner as Example 1(c).

5-Amino-2-cyclohexyl-6-diethylaminobenzo[d]imidazole

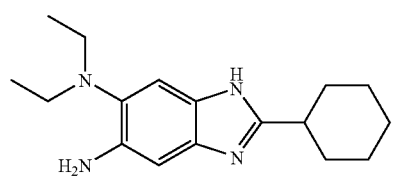

Yield 55%; ¹HNMR (300 MHz, CDCl₃) δ 7.31 (s, 1H), 6.9 (s, 1H), 2.92 (m, 4H, J=10.8 Hz), 2.04 (m, 2H), 1.68 (m, 5H), 1.26 (m, 4H), 0.95 (t, 6H, J=6.9 Hz); ESI MS m/z 287.4 [M+H]⁺.

5-Amino-6-diethylamino-2-(4-methylphenyl)-1H-benzo[d]imidazole

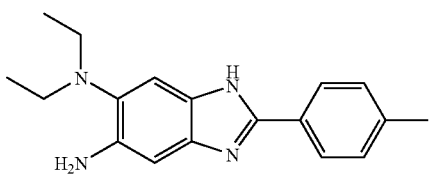

Yield 46%; ¹HNMR (400 MHz, CDCl₃) δ 7.95 (d, J=4.2 Hz, 2H), 7.21 (s, 1H), 7.12 (d, 2H, J=4 Hz), 6.77 (s, 1H), 2.84 (q, 4H, J=10.6 Hz), 2.3 (s, 3H), 0.90 (t, 6H, J=7 Hz); ESI MS m/z 295.3 [M+H]⁺.

5-Amino-6-diethylamino-2-(2-methoxyphenyl)-1H-benzo[d]imidazole

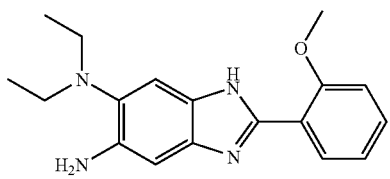

Yield 52%; ¹HNMR (400 MHz, CDCl₃) δ 8.48 (dd, 1H), 7.37-7.29 (m, 2H), 7.48 (t, 1H, J=8 Hz), 6.97 (d, 1H, J=4.2 Hz), 6.88 (s, 1H), 3.96 (s, 3H), 2.96 (q, 4H, J=10.6 Hz), 0.97 (t, 6H, J=7 Hz); ESI MS m/z 311.3 [M+H]⁺.

5-Amino-6-diethylamino-2-(4-tert-butylphenyl)-1H-benzo[d]imidazole

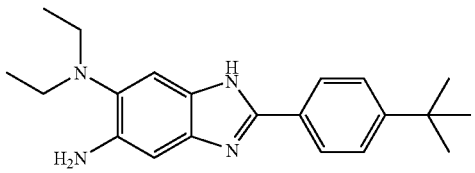

Yield 50%; ¹HNMR (400 MHz, CDCl₃) δ 8.01 (d, 2H, J=2.5 Hz), 7.35 (d, 2H, J=2.5 Hz), 7.29 (s, 1H), 6.78 (s, 1H), 2.86 (q, 4H, J=10.6 Hz), 1.27 (s, 9H), 0.91 (t, 6H, J=7 Hz); ESI MS m/z 337.4 [M+H]⁺.

5-Amino-2-cyclohexyl-6-(piperidin-1-yl)-1H-benzo[d]imidazole

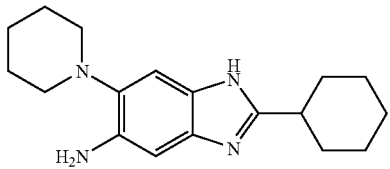

Yield 66%; ¹HNMR (300 MHz, CDCl₃) δ 7.23 (s, 1H), 6.81 (s, 1H), 2.81 (t, 4H, J=4.9 Hz), 2.04 (m, 1H), 1.78-1.23 (m, 16H); ESI MS m/z 299.4 [M+H]⁺.

Examples 35-48

The following key intermediates were prepared and characterized in the same manner as Examples 9-11.

2-Cyclohexyl-6-diethylamino-5-(4-methoxybenzoyl)amino-1H-[d]benzimidazole

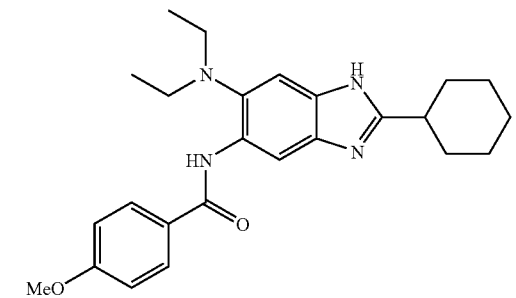

Yield 78%; ¹HNMR (300 MHz, CDCl₃) δ 10.31 (s, 1H), 8.94 (s, 1H), 7.95 (d, 2H, J=4.35 Hz), 7.57 (s, 1H), 7.05 (d, 2H, J=4.35 Hz), 3.9 (s, 3H), 3.0 (m, 4H), 2.1 (s, 1H), 1.98 (m, 2H), 1.58 (m, 5H), 1.26 (m, 3H), 0.97 (t, 6H, J=7.2 Hz); ESI MS m/z 421.5 [M+H]⁺.

5-Benzoylamino-2-cyclohexyl-6-diethylamino-1H-benzo[d]imidazole

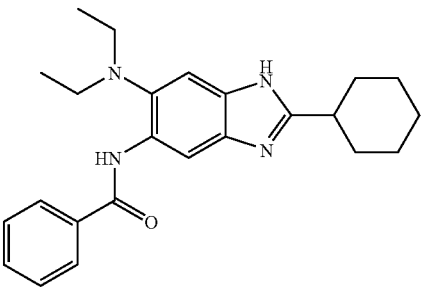

Yield 74%; ¹HNMR (300 MHz, CDCl₃) δ 10.3 (s, 1H), 8.96 (s, 1H), 7.98 (m, 2H), 7.57 (m, 4H), 3.03 (m, 4H, J=10.65 Hz), 1.98 (m, 2H), 1.65 (m, 5H), 1.16 (m, 4H), 0.97 (m, 6H, J=7.2 Hz); ESI MS m/z 391.5 [M+H]⁺.

2-Cyclohexyl-6-diethylamino-5-(4-methylbenzoyl)amino-1H-benzo[d]imidazole

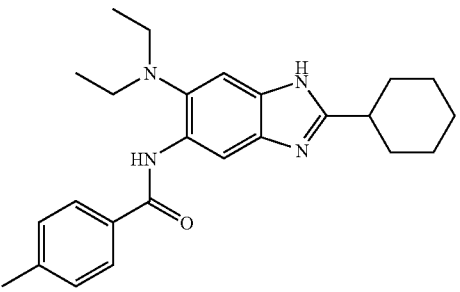

Yield 65%; ¹HNMR (300 MHz, CDCl₃) δ 10.31 (s, 1H), 8.91 (s, 1H), 7.87 (d, 2H, J=4.5 Hz), 7.59 (s, 1H), 7.34 (d, 2H, J=4.2 Hz), 3.02 (m, 4H, J=10.8 Hz), 2.45 (s, 3H), 2.01 (m, 2H), 1.69 (m, 5H), 1.2 (m, 4H), 0.97 (m, 6H, J=7 Hz) ESI MS m/z 405.5 [M+H]⁺.

5-(4-Chlorobenzoyl)amino-2-cyclohexyl-6-diethylamino-1H-benzo[d]imidazole

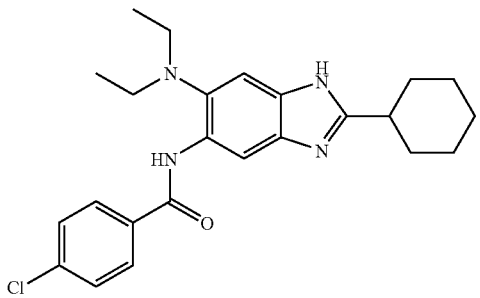

Yield 64%; ¹HNMR (300 MHz, CDCl₃) δ 10.26 (s, 1H), 8.77 (s, 1H), 7.88 (d, 2H, J=3.45 Hz), 7.60 (s, 1H), 7.50 (d, 2H, J=4.2 Hz), 3.02 (m, 4H, J=10.65 Hz), 2.11 (m, 2H), 1.84-1.25 (m, 9H), 0.97 (t, 6H, J=7.2 Hz); ESI MS m/z 425 [M+H]⁺.

5-Benzyloxycarbonylamino-2-cyclohexyl-6-diethylamino-1H-benzo[d]imidazole

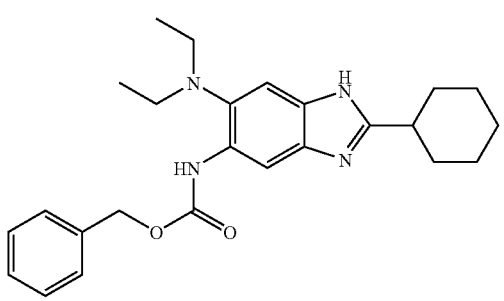

Yield 61%; ¹HNMR (300 MHz, CDCl₃) δ 8.61 (s, 1H), 8.25 (s, 1H), 7.45-7.35 (m, 5H), 5.22 (s, 2H), 2.91 (m, 4H, J=10.65 Hz), 2.11 (m, 2H), 1.84-1.62 (m, 5H), 1.38 (m, 4H), 0.90 (t, 6H, J=7.2 Hz); ESI MS m/z 421.5 [M+H]⁺.

2-Cyclohexyl-6-diethylamino-5-propoxycarbonylamino-1H-benzo[d]imidazole

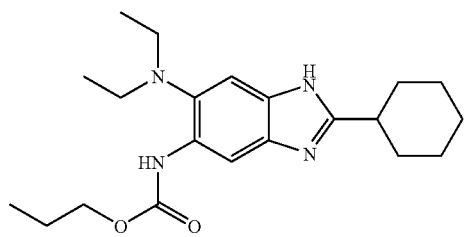

Yield 63%; ¹HNMR (300 MHz, CDCl₃) δ 8.51 (s, 1H), 8.23 (s, 1H), 7.47 (s, 1H), 4.14 (t, 2H, J=6.75 Hz), 2.92 (m, 4H, J=10.8 Hz), 2.10 (m, 2H), 1.87-1.60 (m, 7 H), 1.40-1.25 (m, 4H), 0.98 (t, 3H, J=6.15 Hz), 0.93 (t, 6H, J=7.05 Hz) ESI MS m/z 373.5 [M+H]⁺.

5-Butoxycarbonylamino-2-cyclohexyl-6-diethylamino-1H-benzo[d]imidazole

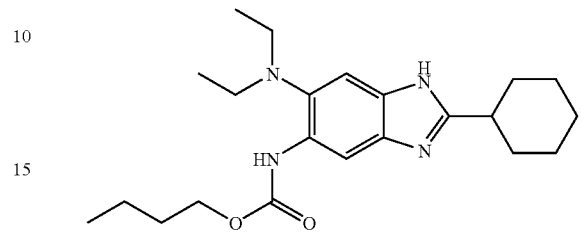

Yield 51%; ¹HNMR (300 MHz, CDCl₃) δ 8.50 (s, 1H), 8.22 (s, 1H), 7.48 (s, 1H), 4.18 (t, J=6.75 Hz, 2H), 2.92 (m, J=10.5 Hz, 4H), 2.10 (m, 2H), 1.87-1.60 (m, 7H), 1.40-1.39 (m, 6H), 0.96 (t, J=7.5 Hz, 3H), 0.92 (t, J=7.2 Hz, 6H); ESI MS m/z 387.5 [M+H]⁺.

5-(But-3-enoxycarbonyl)amino-2-cyclohexyl-6-diethylamino-1H-benzo[d]imidazole

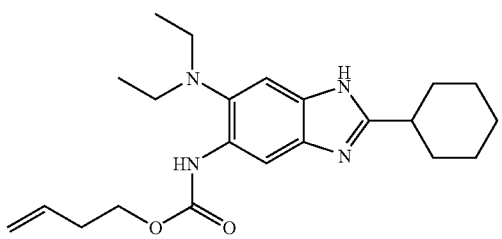

Yield 51%; ¹HNMR (300 MHz, CDCl₃) δ 8.51 (s, 1H), 8.23 (s, 1H), 7.48 (s, 1H), 5.84 (m, 1H), 5.11 (m, 2H), 4.23 (t, 2H, J=6.9 Hz), 2.92 (m, 4H, J=10.5 Hz), 2.47 (t, 2H, J=4.65 Hz), 2.10 (m, 2H), 1.82-1.60 (m, 5H), 1.40-1.32 (m, 4H), 0.91 (t, 6H, J=7.05 Hz); ESI MS m/z 385.2 [M+H]⁺.

5-(4-tert-Butylbenzoylamino)-2-cyclohexyl-6-diethylamino-1H-benzo[d]imidazole

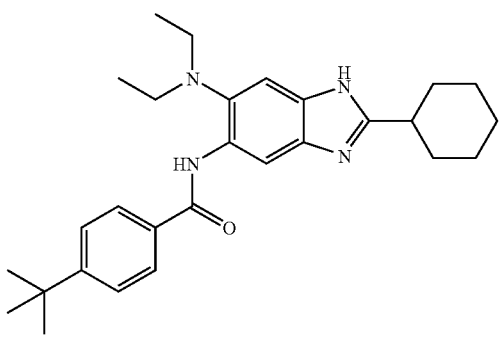

Yield 48%; ¹HNMR (400 MHz, CDCl₃) δ 10.41 (s, 1H), 9.02 (s, 1H), 7.93 (d, 2H, J=4.2 Hz), 7.57 (d, 3H, J=4.2 Hz), 3.02 (q, 4H, J=10.6 Hz), 2.68 (m, 1H), 1.92 (m, 2H), 1.67-

1.53 (m, 5H), 1.38 (s, 9H), 1.24 (s, 2H), 1.26 (m, 3H), 0.97 (t, 6H, J=7 Hz); ESI MS m/z 2447.6 [M+H]⁺.

2-Cyclohexyl-5-cyclopentanecarbonylamino-6-diethylamino-1H-benzo[d]imidazole

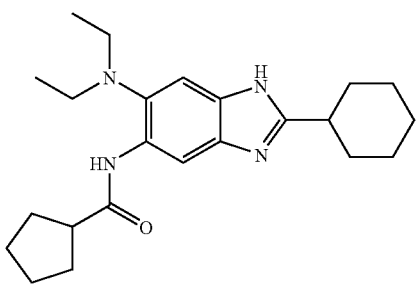

Yield 74%; ¹HNMR (400 MHz, CDCl₃) δ 9.41 (s, 1H), 8.65 (s, 1H), 7.50 (s, 1H), 2.93 (q, 4H, J=10.6 Hz), 2.81 (m, 2H), 2.07-1.67 (m, 15H), 1.31 (m, 3H), 0.92 (t, 6H, J=7 Hz); ESI MS m/z 383.5 [M+H]⁺.

2-Cyclohexyl-6-diethylamino-5-(3-phenylpropanoyl)amino-1H-benzo[d]imidazole

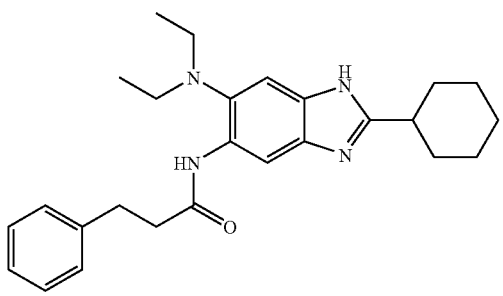

Yield 55%; ¹HNMR (400 MHz, CDCl₃) δ 9.33 (s, 1H), 8.69 (s, 1H), 7.49 (s, 1H), 7.59 (s, 1H), 7.27-7.18 (m, 5H), 3.11 (t, 2H, J=7.6 Hz), 2.86 (q, 3H, J=10.6 Hz), 2.76 (t, 2H, J=7.6 Hz), 2.08 (m, 2H), 1.8-1.6 (m, 4H), 1.35-1.23 (m, 5H), 0.83 (t, 6H, J=7 Hz); ESI MS m/z 419.5 [M+H]⁺.

2-Cyclohexyl-6-diethylamino-5-pentanoylamino-1H-benzo[d]imidazole

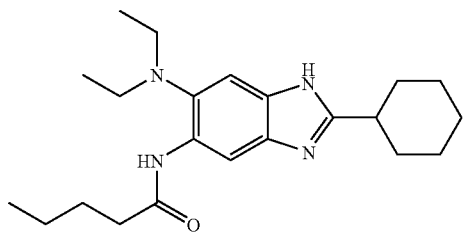

Yield 60%; ¹HNMR (3\400 MHz, CDCl₃) δ 9.45 (s, 1H), 8.73 (s, 1H), 7.51 (s, 1H), 2.94 (q, 4H, J=10.9 Hz), 2.84 (m, 1H), 2.49 (t, 2H, J=7.6 Hz), 2.10 (m, 2H), 1.84-1.65 (m, 7H), 1.48-1.25 (m, 5H), 0.96 (t, 3H, J=7.4 Hz), 0.92 (t, 6H, J=7.2 Hz); ESI MS m/z 371.5 [M+H]⁺.

5-Butanoylamino-2-cyclohexyl-6-diethylamino-1H-benzo[d]imidazole

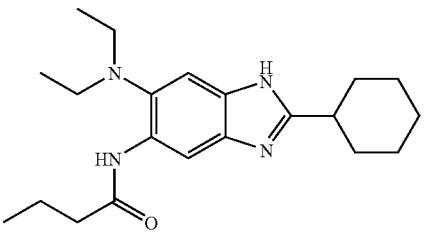

Yield 75%; ¹HNMR (400 MHz, CDCl₃) δ 9.45 (s, 1H), 8.73 (s, 1H), 7.52 (s, 1H), 2.94 (q, 4H, J=10.8 Hz), 2.84 (m, 1H), 2.45 (t, 2H, J=7.6 Hz), 2.10 (m, 2H), 1.84-1.65 (m, 7H), 1.48-1.25 (m, 5H), 1.06 (t, 3H, J=7.4 Hz), 0.92 (t, 6H, J=7.2 Hz); ESI MS m/z 357.5 [M+H]⁺.

2-Cyclohexyl-6-diethylamino-5-(prop-2-enoxycarbonyl)amino-1H-benzo[d]imidazole

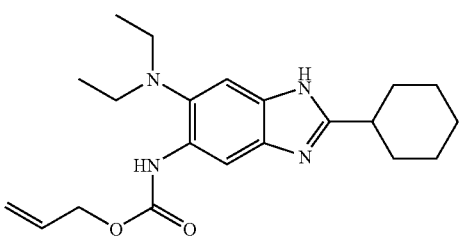

Yield 51%; ¹HNMR (300 MHz, CDCl₃) δ 8.51 (s, 1H), 8.23 (s, 1H), 7.48 (s, 1H), 5.84 (m, 1H), 5.11 (m, 2H), 4.23 (t, 2H, J=6.9 Hz), 2.92 (q, 4H, J=10.5 Hz), 2.47 (t, 2H, J=4.65 Hz), 2.10 (m, 2H), 1.82-1.6 (m, 5H), 1.40-1.32 (m, 4H), 0.91 (t, 6H, J=7.05 Hz); ESI MS m/z 371.4 [M+H]⁺.

Examples 49-54

The following key intermediates 49 through 54 were prepared and characterized in the same manner as 7-amino-5-(methoxycarbonyl)amino-2-(4-bromophenyl)-1H-benzo[d]imidazole in Example 12(b).

7-Amino-5-ethoxycarbonylamino-2-(furan-2-yl)-1H-benzo[d]imidazole

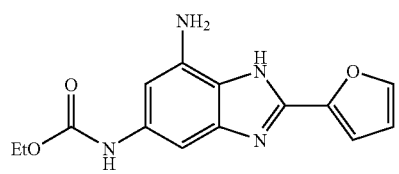

Yield 55%; ¹H-NMR (300 MHz, CD₃OD) δ 1.29 (t, 3H, J=9 Hz), 4.16 (dd, 2H, J=14.1, 7.2 Hz), 6.51 (s, 1H), 6.61 (m, 1H), 7.05 (m, 1H), 7.13 (s, 1H), 7.67 (m, 1H); ESI MS m/z 287.0 [M+H]⁺.

7-Amino-5-methoxycarbonylamino-2-(4-methoxycarbonylphenyl)-1H-benzo[d]imidazole

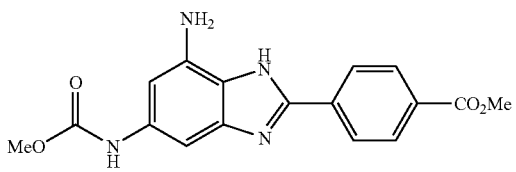

Yield 57%; ¹H-NMR (300 MHz, CD₃OD) δ 3.73 (s, 3H), 3.93 (s, 3H), 6.52 (s, 1H), 7.19 (s, 1H), 8.12 (s, 4H); ESI MS m/z 341.0 [M+H]⁺.

7-Amino-5-ethoxylcarbonylamino-2-phenyl-1H-benzo[d]imidazole

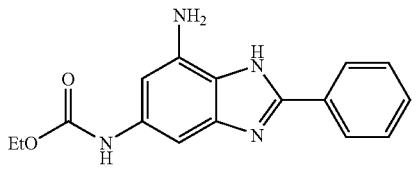

Yield 54%; ¹H-NMR (300 MHz, CD₃OD) δ 1.30 (t, 3H, J=6.9 Hz), 4.16 (dd, 2H, J=14.4, 7.2 Hz), 6.51 (s, 1H), 7.18 (s, 1H), 7.44 (m, 3H), 8.01 (m, 2H); ESI MS m/z 297.1 [M+H]⁺.

7-Amino-2-(2,4-dimethoxyphenyl)-5-methoxycarbonylamino-1H-benzo[d]imidazole

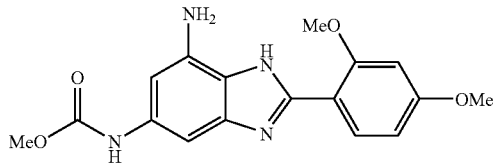

Yield 53%: ¹H-NMR (300 MHz, CD₃OD) δ 3.72 (s, 3H), 3.85 (s, 3H), 3.99 (s, 3H), 6.51 (s, 1H), 6.66 (m, 2H), 7.17 (bs, 1H), 8.06 (d, 1H, J=9.3 Hz); ESI MS m/z 343.0 [M+H]⁺.

7-Amino-2-(3-fluorophenyl)-5-methoxycarbonylamino-1H-benzo[d]imidazole

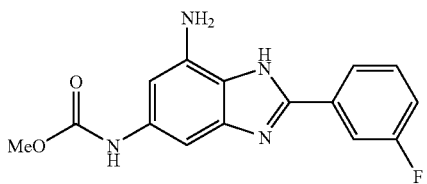

Yield 50%: ¹H-NMR (300 MHz, CD₃OD) δ 3.72 (s, 3H), 6.51 (s, 1H), 7.17 (m, 2H), 7.50 (m, 1H), 7.78 (m, 2H); ESI MS m/z 301.1 [M+H]⁺.

7-Amino-5-ethoxycarbonylamino-2-(phenylamino)-1H-benzo[d]imidazole

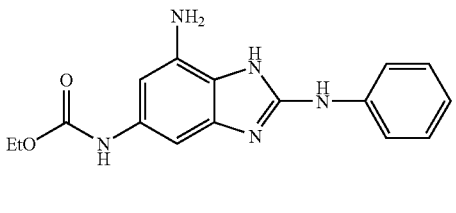

Yield 52%; ¹H-NMR (300 MHz, CD₃OD) δ 1.30 (t, 3H, J=7.2 Hz), 4.14 (dd, 2H, J=14.1, 7.2 Hz), 6.48 (s, 1H), 6.95 (m, 1H), 7.27 (t, 2H), 7.43 (m, 2H); ESI MS m/z 311.9 [M+H]⁺.

Examples 55-56

The following key intermediates 55 and 56 were prepared and characterized in the same manner as 7-acetylamino-5-(methoxycarbonyl)amino-2-(4-bromophenyl)-1H-benzo[d]imidazole in Example 12 (c).

7-Acetylamino-5-ethoxycarbonylamino-2-phenyl-1H-benzo[d]imidazole

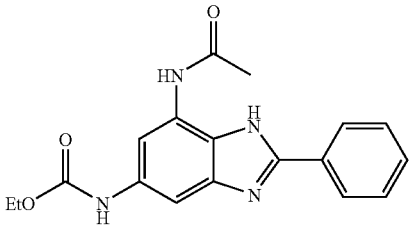

Yield 85%; ¹H-NMR (300 MHz, CD₃OD) δ 1.30 (t, 3H, J=7.2 Hz), 2.32 (s, 3H), 4.24 (dd, 2H, J=14.4, 7.2 Hz), 7.58 (m, 3H), 7.77 (bs, 1H), 7.85 (bs, 1H), 8.10 (m, 2H); ESI MS m/z 339.1 [M+H]⁺.

7-Acetylamino-2-(3-fluorophenyl)-5-methoxycarbonylamino-1H-benzo[d]imidazole

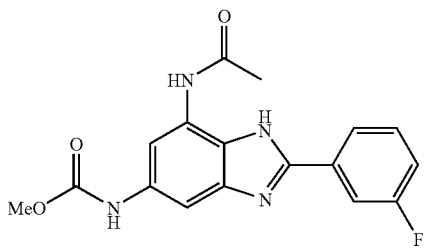

Yield 83%: ¹H-NMR (300 MHz, CD₃OD) δ 2.25 (s, 3H), 3.74 (s, 3H), 6.51 (s, 1H), 7.22 (m, 1H), 7.52 (m, 1H), 7.78 (m, 5H); ESI MS m/z 343.1 [M+H]⁺.

APPENDIX
Active Benzimidazole Derivatives
SB-P2B5
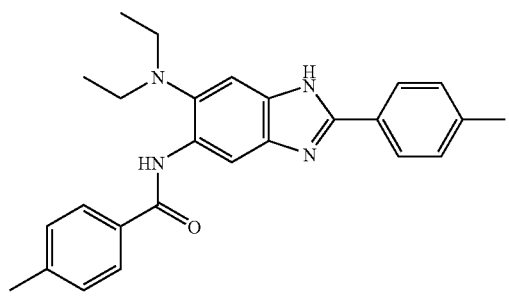
SB-P3B2
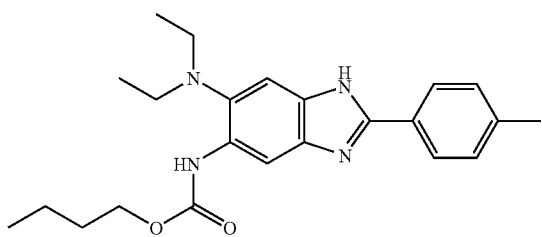
SB-P3B5
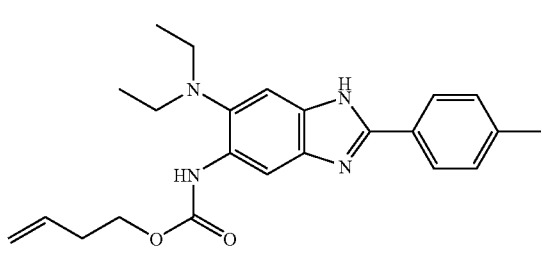
SB-P1D4
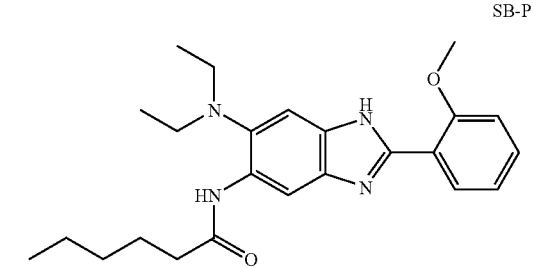
SB-P1D7
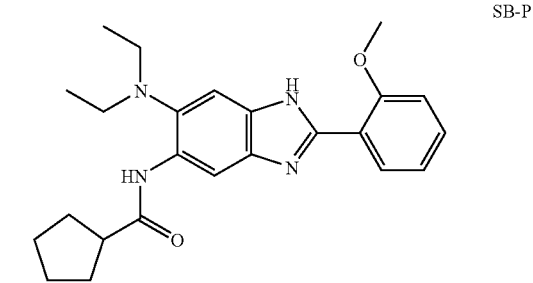
SB-P3F1
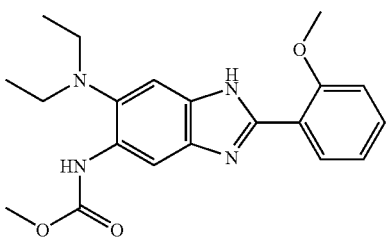
SB-P1G2
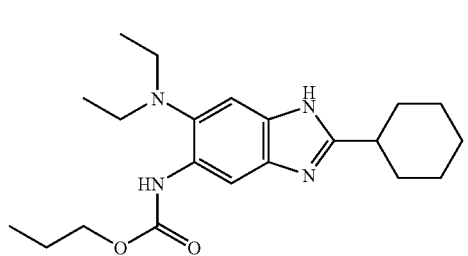
SB-P1G3
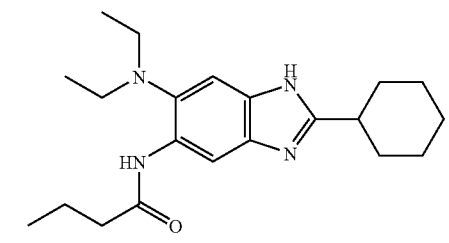
SB-P1G4
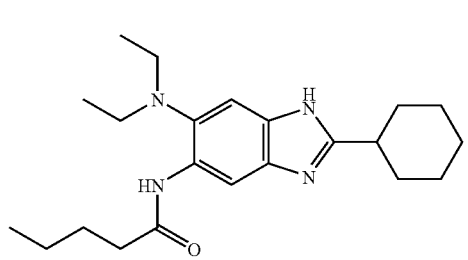
SB-P1G7
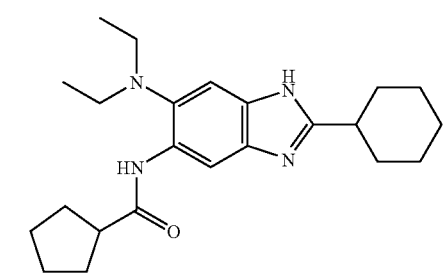
SB-P1G8
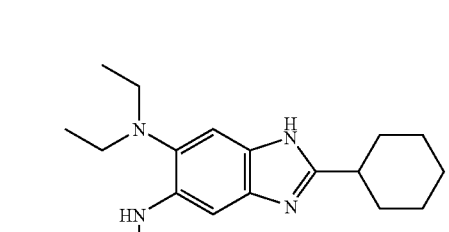

SB-P1G10
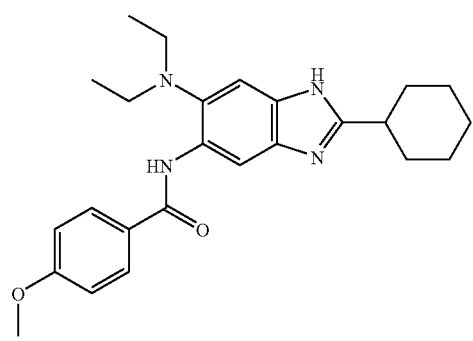
SB-P2G1
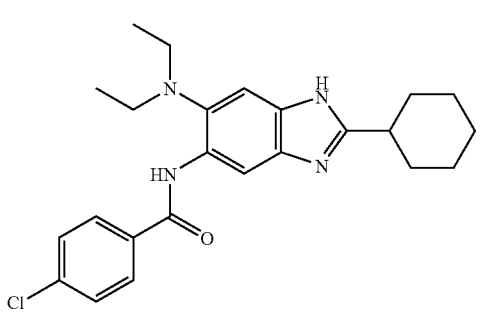
SB-P2G2
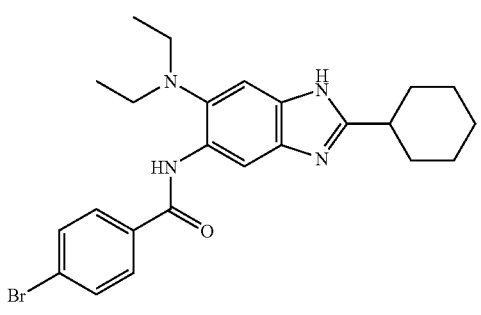
SB-P2G3
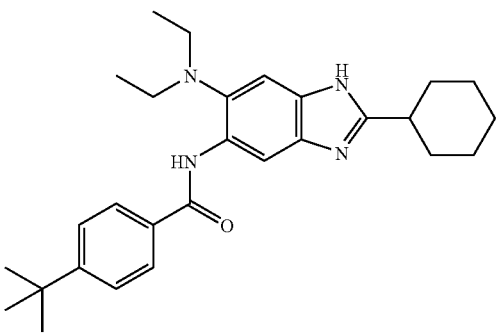
SB-P2G5
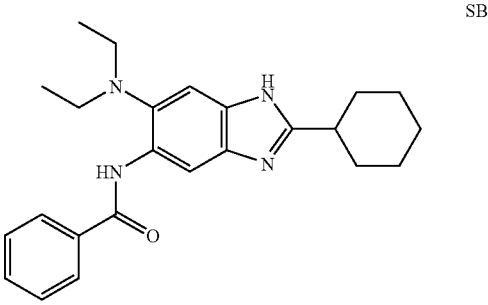
SB-P2G6
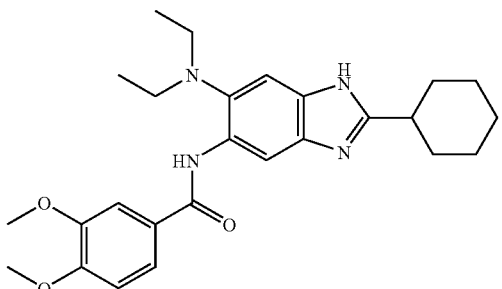
SB-P2G11
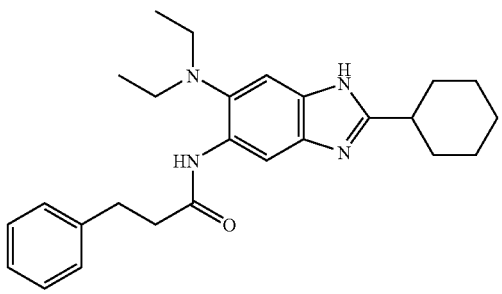
SB-P3G1
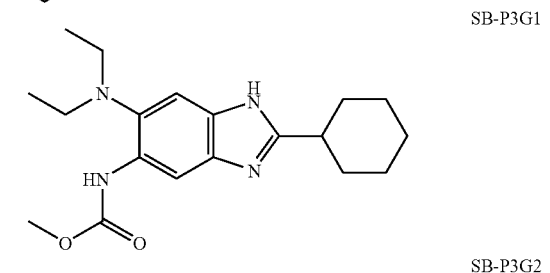
SB-P3G2
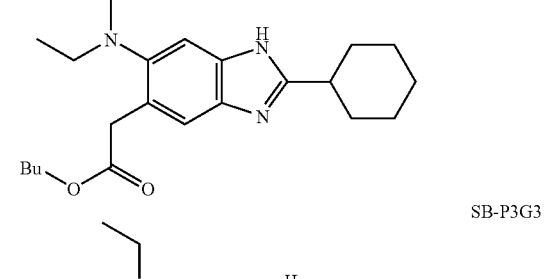
SB-P3G3
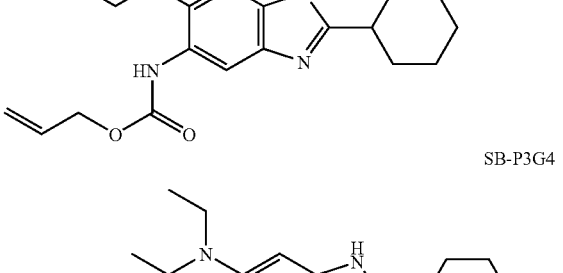
SB-P3G4
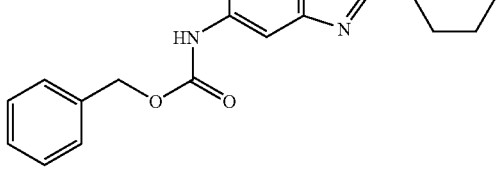

-continued

SB-P3G5

SB-P2H5

SB-P2H3

SB-P1B4

SB-P1D8

-continued

SB-P1D10

SB-P2B6

SB-P3B4

SB-P3F2

SB-P3F3

-continued
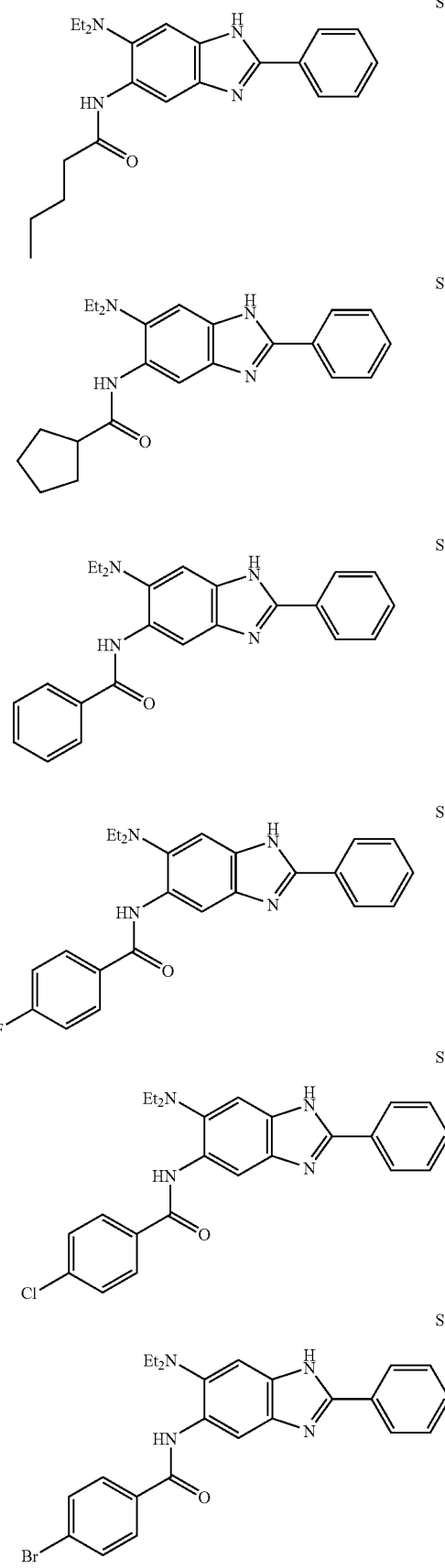
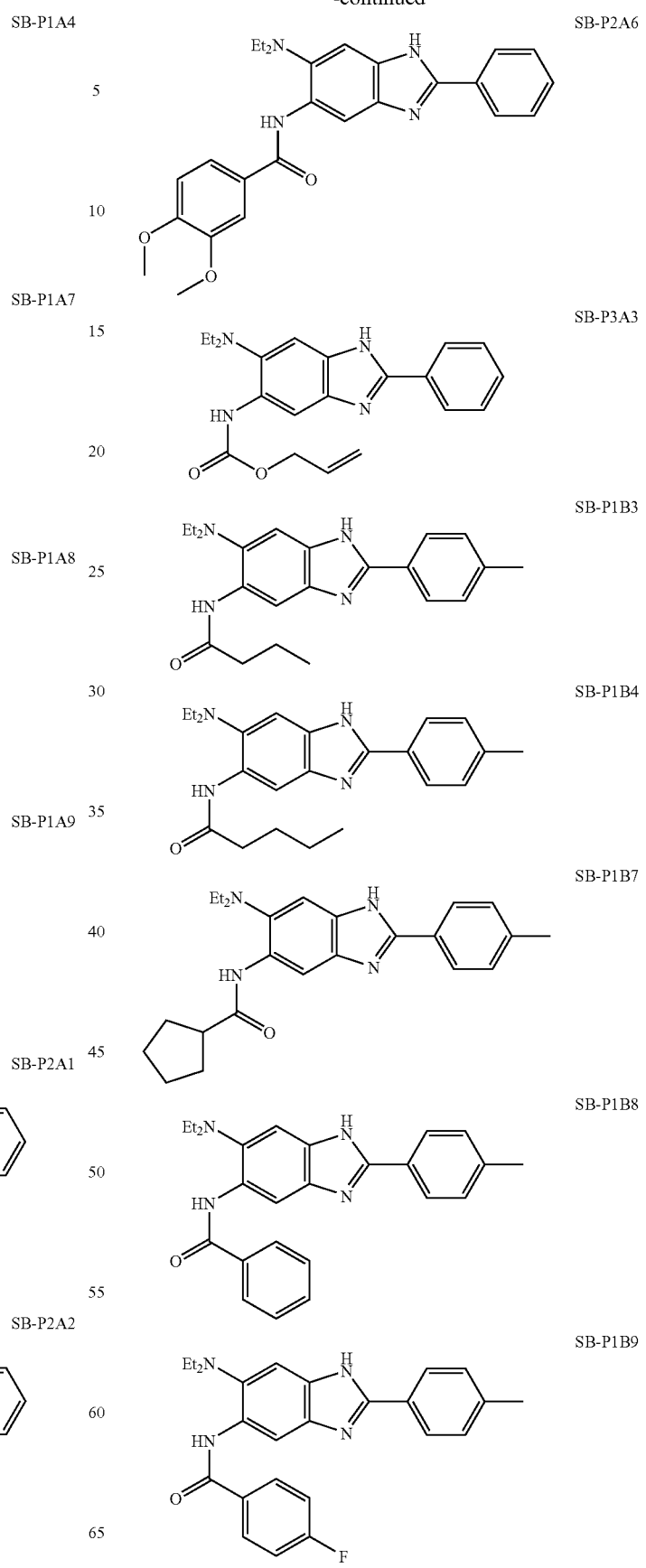

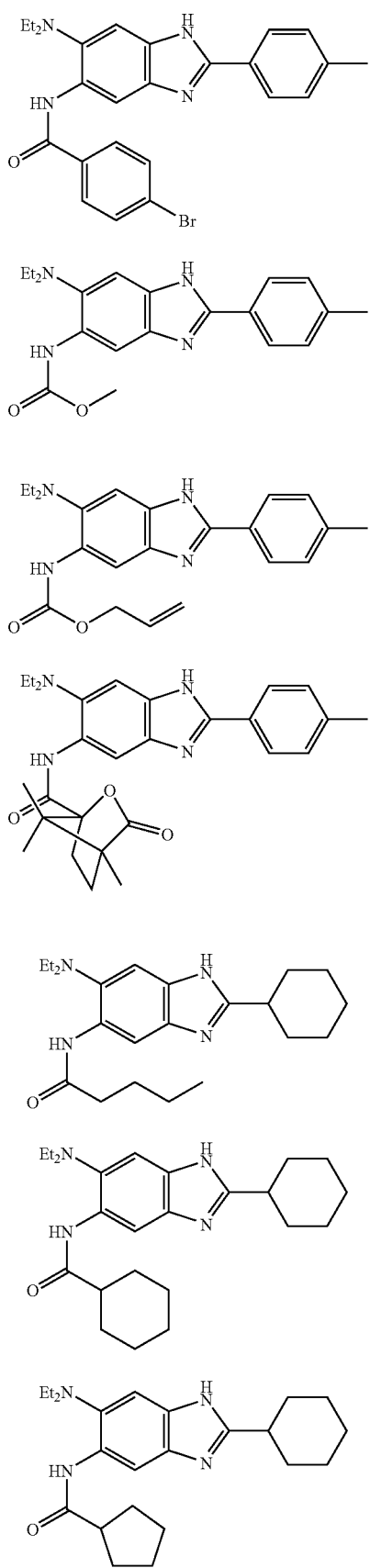
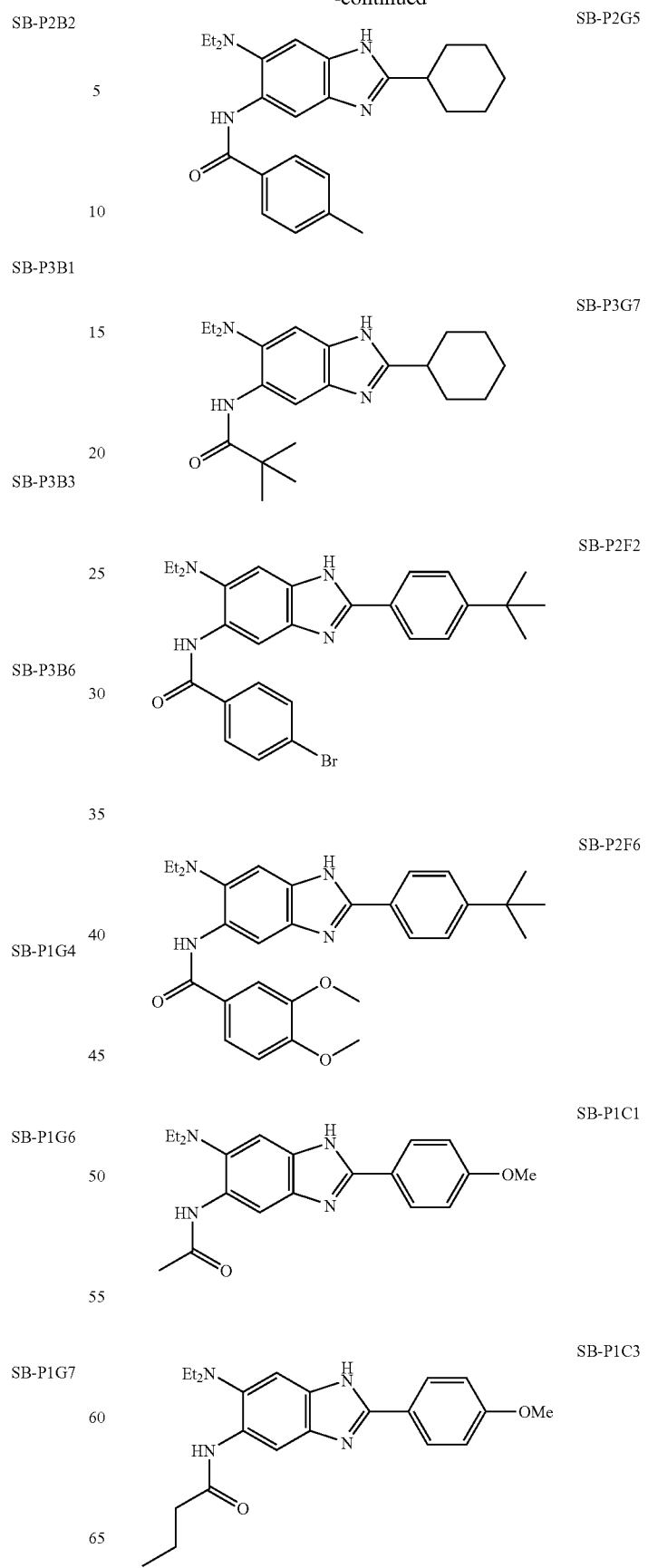

-continued
SB-P1C4
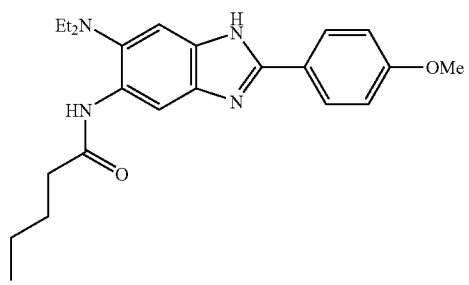
SB-P1C6
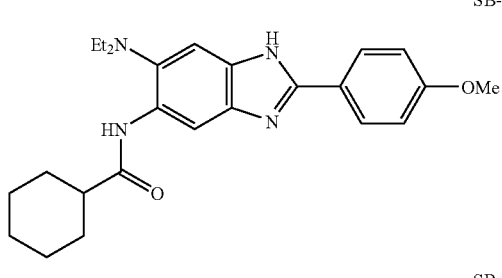
SB-P1C7
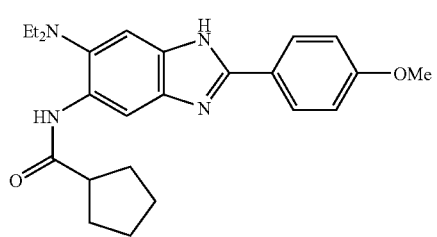
SB-P1C8
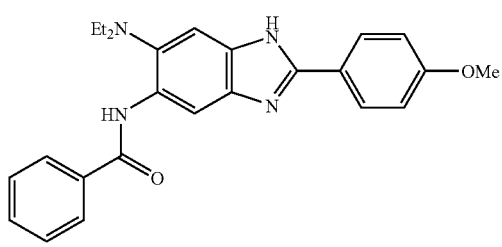
SB-1C9
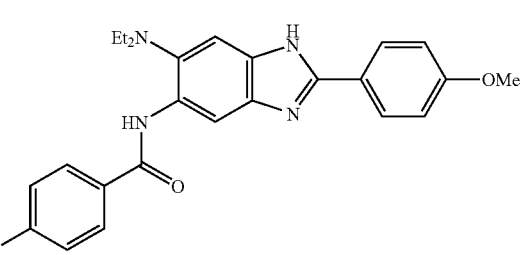
SB-P1C10
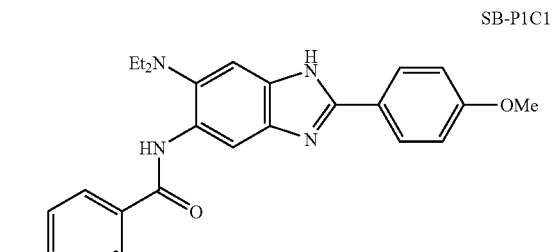
-continued
SB-P2C1
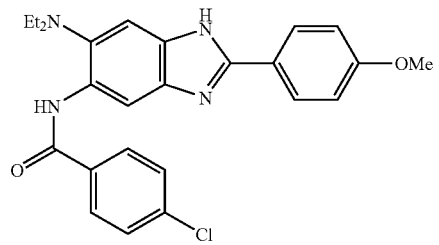
SB-P2C2
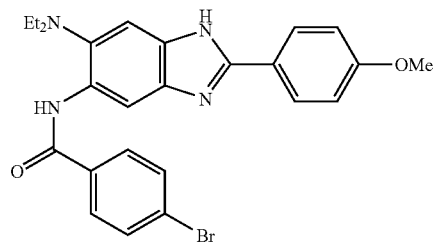
SB-P2C5
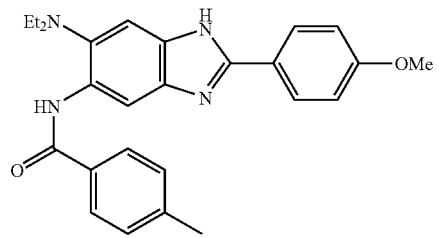
SB-P3C3
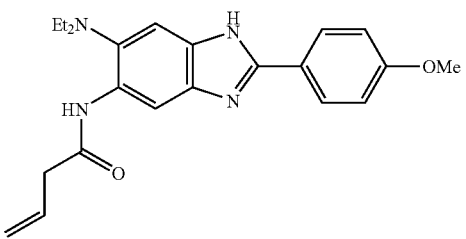
SB-P3C6
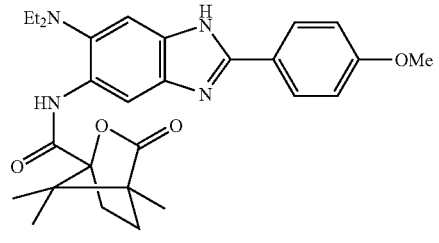
SB-P3C8
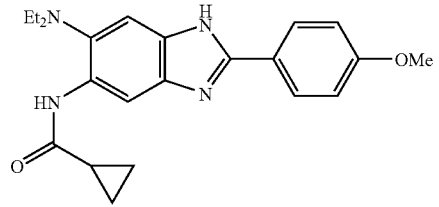
SB-P1E1
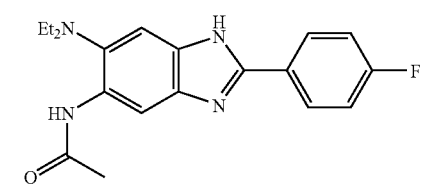

SB-P1E2
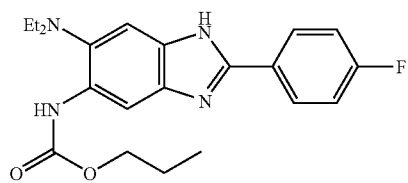
SB-P1E3
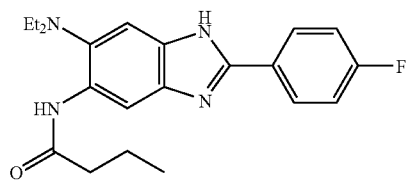
SB-P1E4
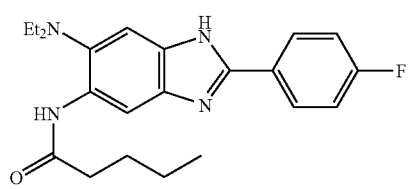
SB-P1E6
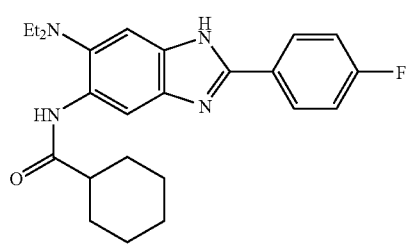
SB-P1E7
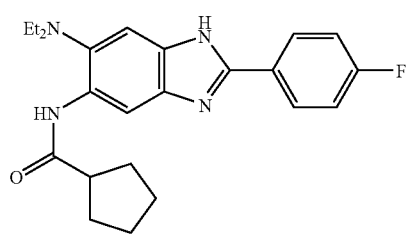
SB-P1E8
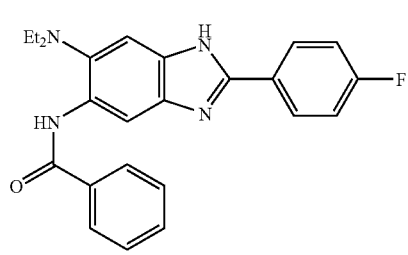
SB-P1E9
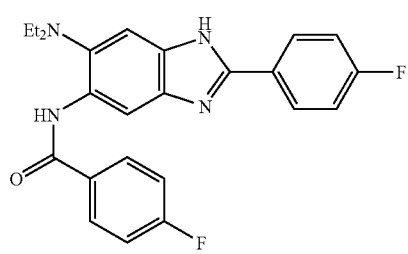
SB-P1E10
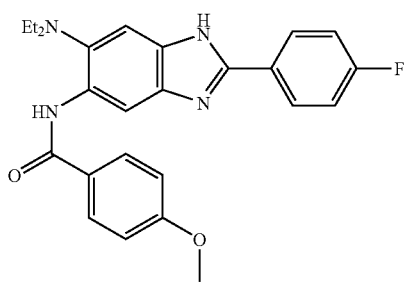
SB-P1E11
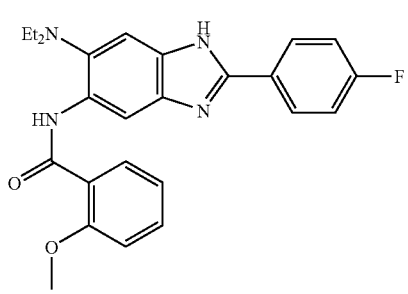
SB-P2E2
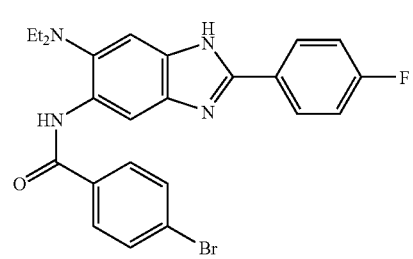
SB-P2F6
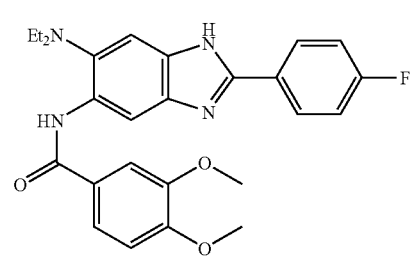
SB-P3E3
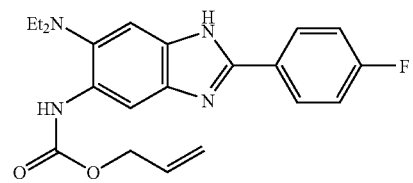
SB-P1D1
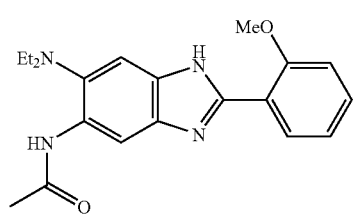

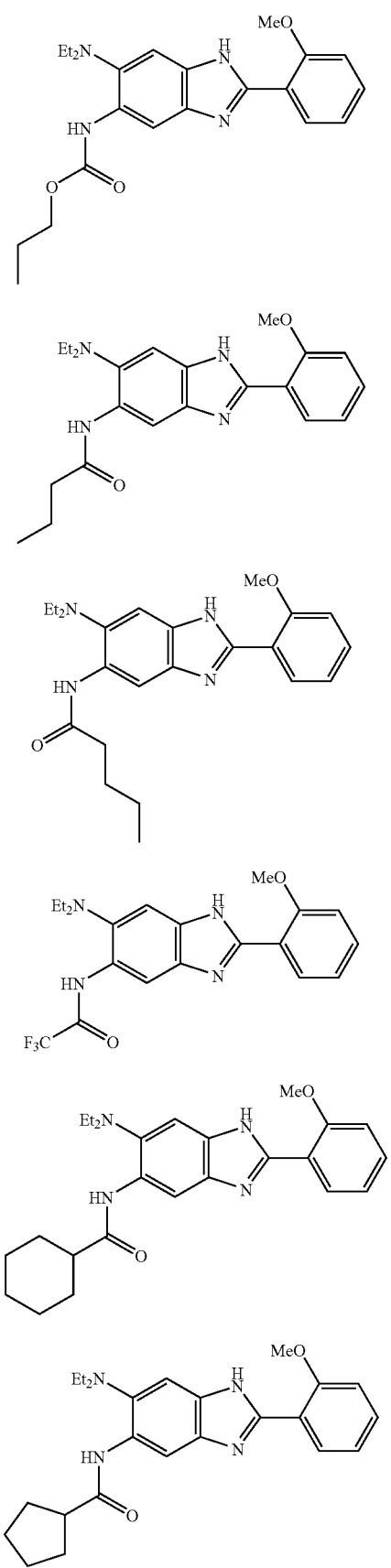
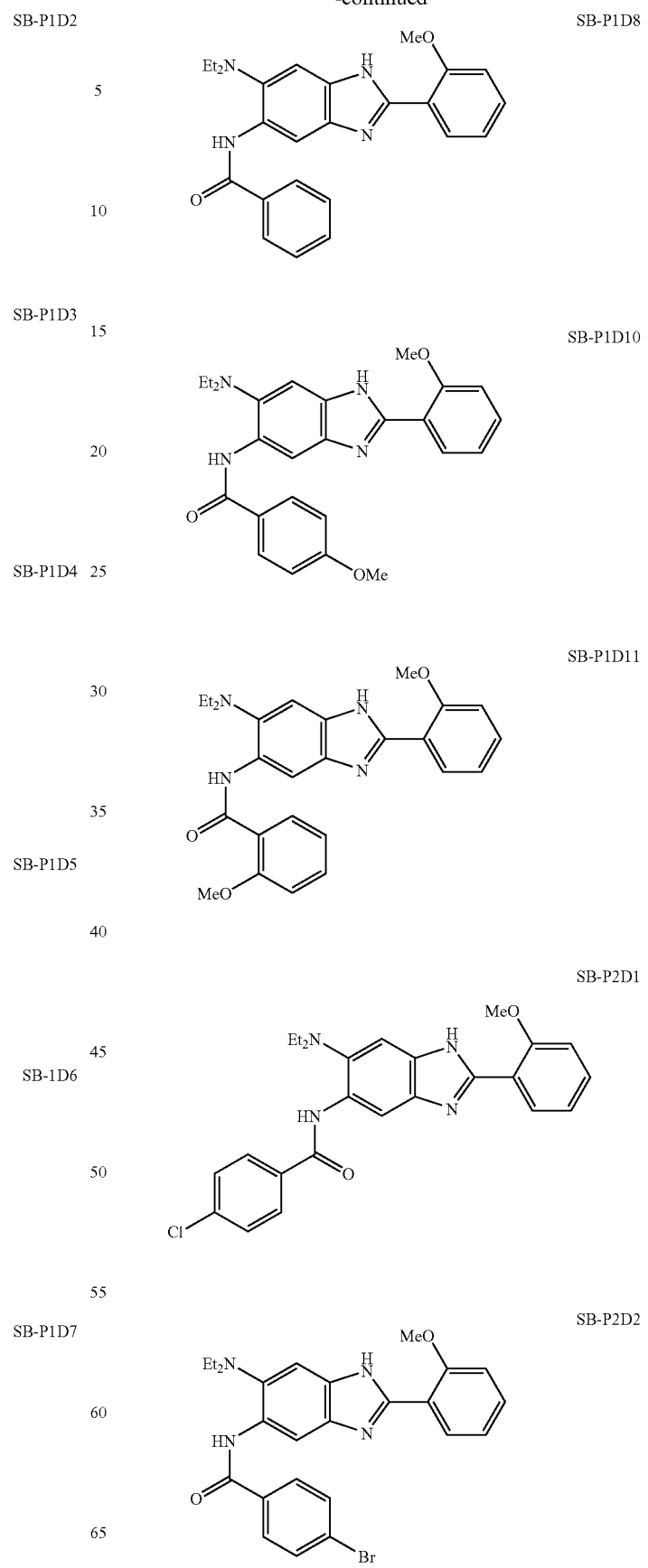

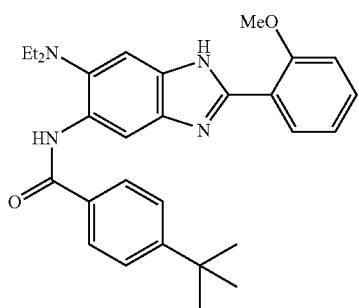 SB-P2D3
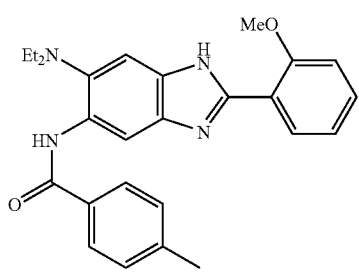 SB-P2D5
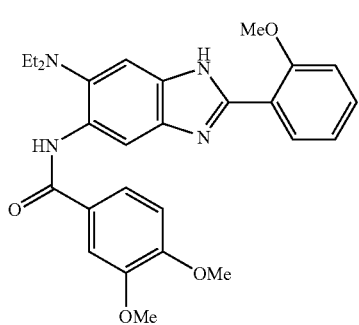 SB-P2D6
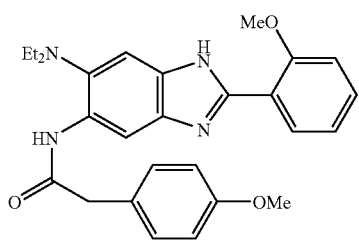 SB-P2D7
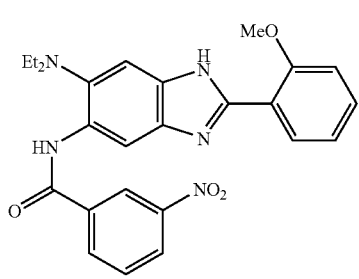 SB-P2D9
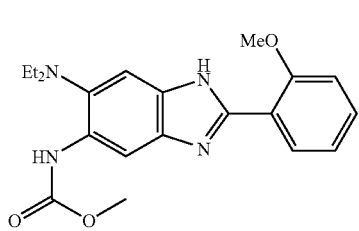 SB-P3D1
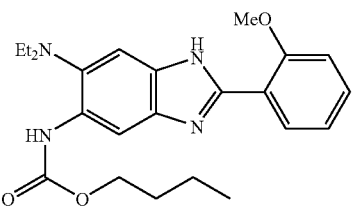 SB-P3D2
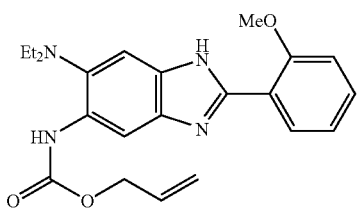 SB-3D3
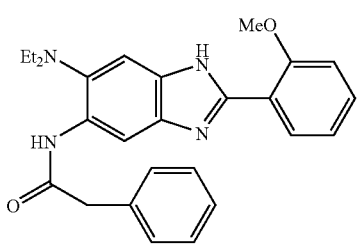 SB-3D4
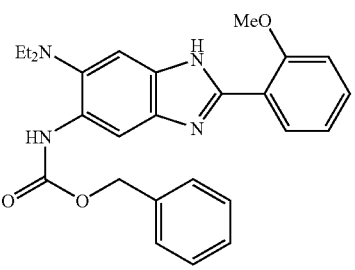 SB-P3D5
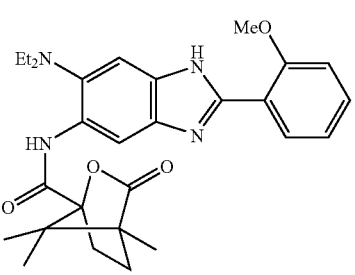 SB-P3D6
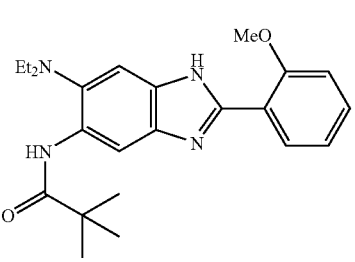 SB-P3D7

We claim:
1. A molecule of formula I wherein:
R$^1$ represents NH$_2$, NHR$^6$, NR$^9$R$^{10}$, NR$^6$CONR$^9$R$^{10}$, NR$^6$CSNR$^9$R$^{10}$, OH, OR$^6$, SH, SR$^6$, CHO, COOR$^6$, COR$^6$, CH$_2$OH, CR$^7$R$^8$OH, CH$_2$OR$^6$, CR$^7$R$^8$OR$^6$, CH$_2$NH$_2$, CR$^7$R$^8$NH$_2$, CR$^7$R$^8$NR$^9$R$^{10}$, alkyl, cycloalkyl, aryl, or halo;
R$^2$ and R$^4$ independently represent H, alkyl, cycloalkyl, or aryl;
R$^3$ represents alkyl, cycloalkyl, or aryl;
R$^5$ represents H, R$^6$, OR$^6$, SR$^6$, NH$_2$, NHR$^6$, or NR$^9$R$^{10}$;
X represents O, S, NH, or NR$^6$;
R$^6$, R$^7$, R$^8$, R$^9$, and R$^{10}$ independently represent alkyl, cycloalkyl, aryl, or halo; or R$^2$ and R$^3$; R$^4$ and R$^5$; and R$^9$ and R$^{10}$ independently, may be combined to represent a heterocyclic alkyl or heterocyclic aryl; or
R$^7$ and R$^8$ may be combined to represent a cycloalkyl;
alkyl groups are branched or unbranched, saturated or unsaturated, and have 1-18 carbon atoms in their longest chain;
cycloalkyl groups are carbocyclic or heterocyclic, fused or unfused, non-aromatic ring systems having a total of 5-16 ring members including substituent rings;
aryl groups are carbocyclic or heterocyclic;
carbocyclic aryl groups are fused or unfused ring systems having a total of 6-16 ring members including substituent rings;
heterocyclic aryl groups are fused or unfused ring systems having a total of 5-16 ring members including substituent rings;
halo substituents are fluoro, chloro, or bromo;
each alkyl, cycloalkyl, and aryl, independently, may be unsubstituted or substituted with one or more substituent at any position;
alkyl substituents are halo, hydroxyl, OR$^6$, SR$^6$, NH$_2$, NHR$^6$, NR$^9$R$^{10}$, cycloalkyl, or aryl;
cycloalkyl substituents are halo, hydroxyl, OR$^6$, SR$^6$, NH$_2$, NHR$^6$, NR$^9$R$^{10}$, alkyl, cycloalkyl, or aryl;
aryl substituents are halo, hydroxyl, OR$^6$, SR$^6$, NH$_2$, NHR$^6$, NR$^9$R$^{10}$, alkyl, cycloalkyl, aryl, nitro, or carboxyl; and
heterocyclic alkyl and heterocyclic aryl have at least one heteroatom selected from oxygen, nitrogen and sulfur; or
a pharmaceutically acceptable salt thereof.

2. A molecule according to claim 1, wherein:
R$^1$ represents cycloalkyl or aryl;
R$^2$ and R$^3$ independently represent C1-C4 alkyl.

3. A molecule according to claim 2, wherein:
R$^4$ is H; and
X is O.

4. A molecule according to claim 2, wherein:
R$^1$ represents

R$^2$ and R$^3$ represent ethyl;
R$^4$ represents H;
R$^5$ represents

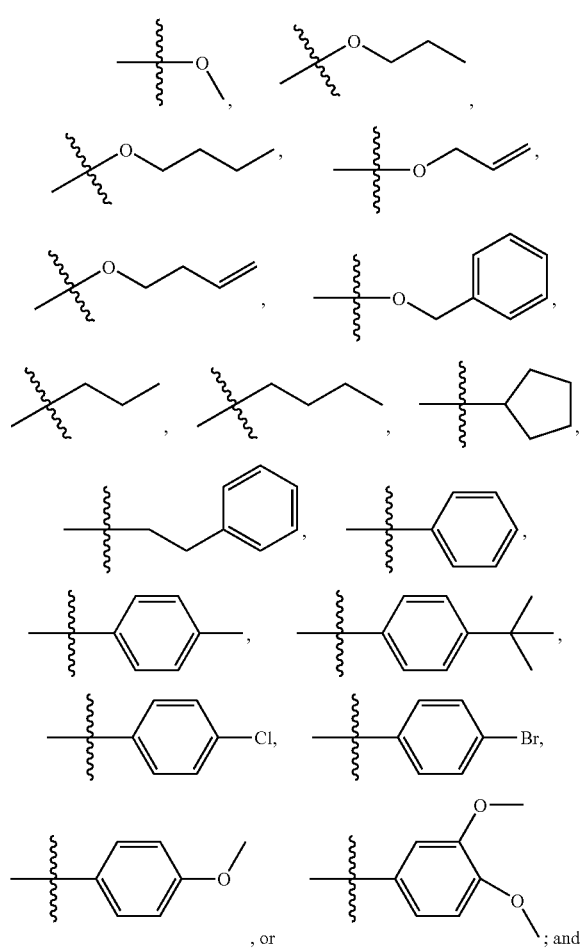
X represents O.
5. A molecule according to claim 2, wherein:
R¹ represents
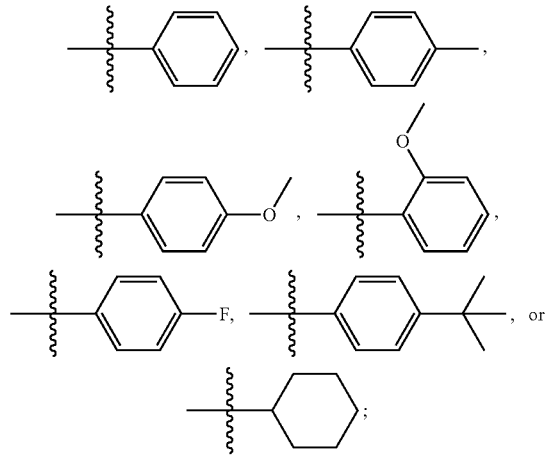
R² and R³ represent ethyl;
R⁴ represents H;
R⁵ represents
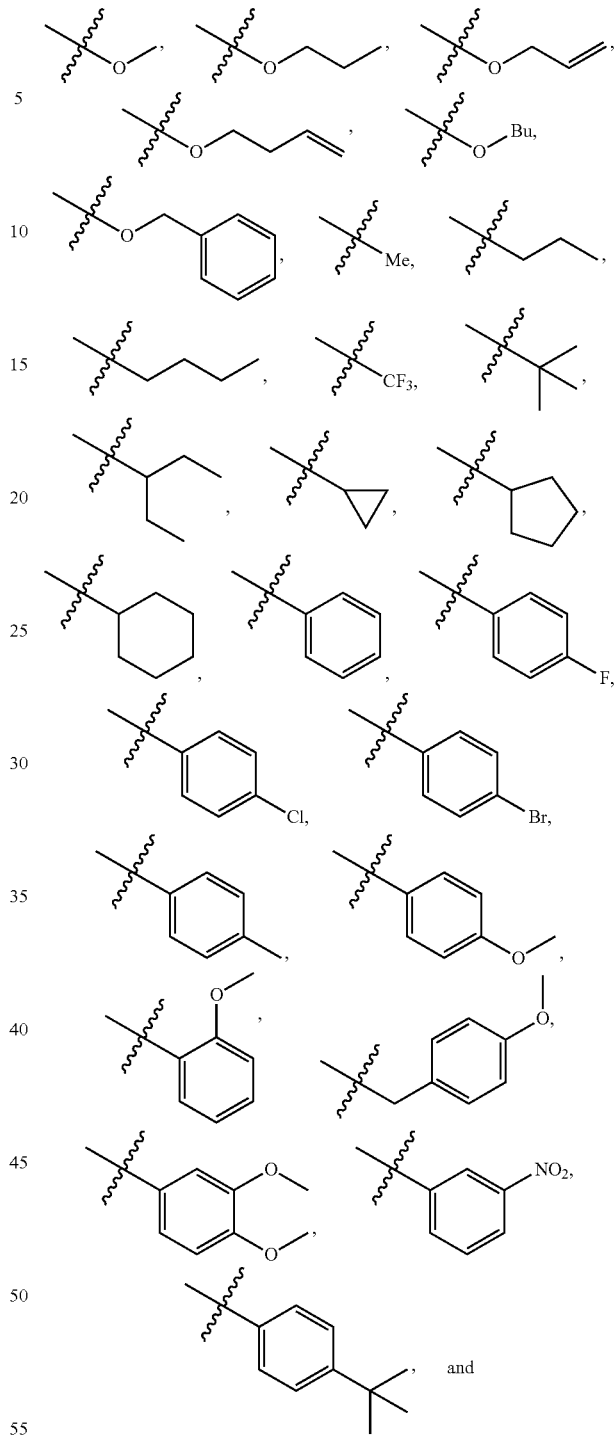
X represents O.
6. A molecule according to claim 5, wherein:
R¹ represents
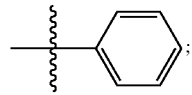

$R^2$ and $R^3$ represent ethyl;
$R^4$ represents H;
$R^5$ represents

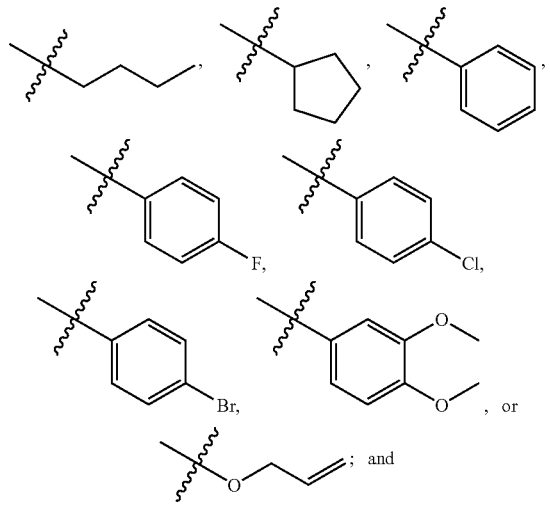

X represents O.

7. A molecule according to claim 5, wherein:
$R^1$ represents

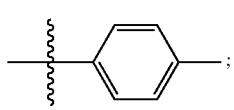

$R^2$ and $R^3$ represent ethyl;
$R^4$ represents H;
$R^5$ represents

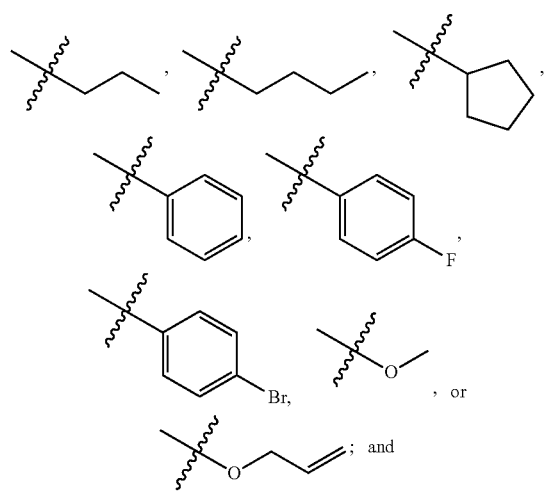

X represents O.

8. A molecule according to claim 5, wherein:
$R^1$ represents

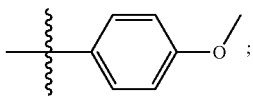

$R^2$ and $R^3$ represent ethyl;
$R^4$ represents H;
$R^5$ represents

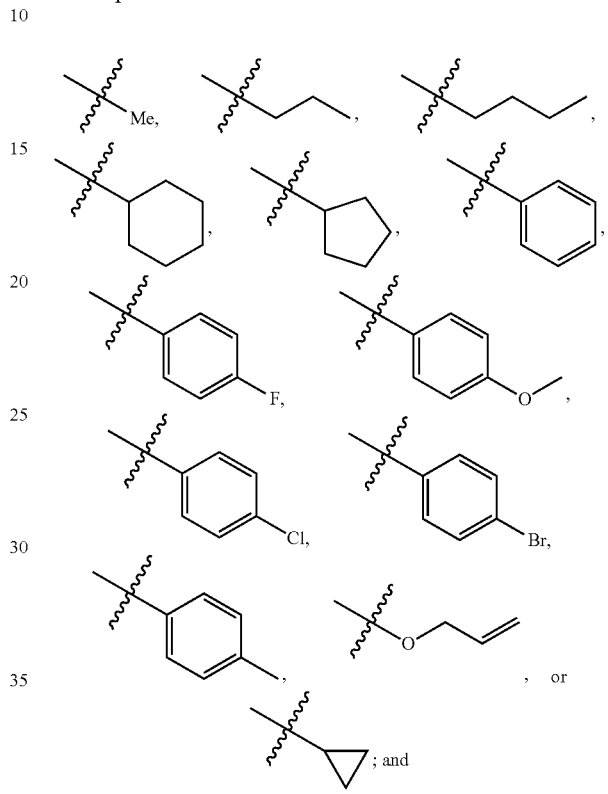

X represents O.

9. A molecule according to claim 5, wherein:
$R^1$ represents

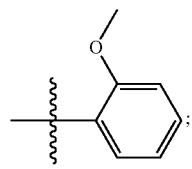

$R^2$ and $R^3$ represent ethyl;
$R^4$ represents H;
$R^5$ represents

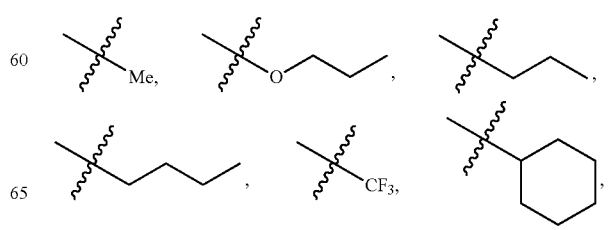

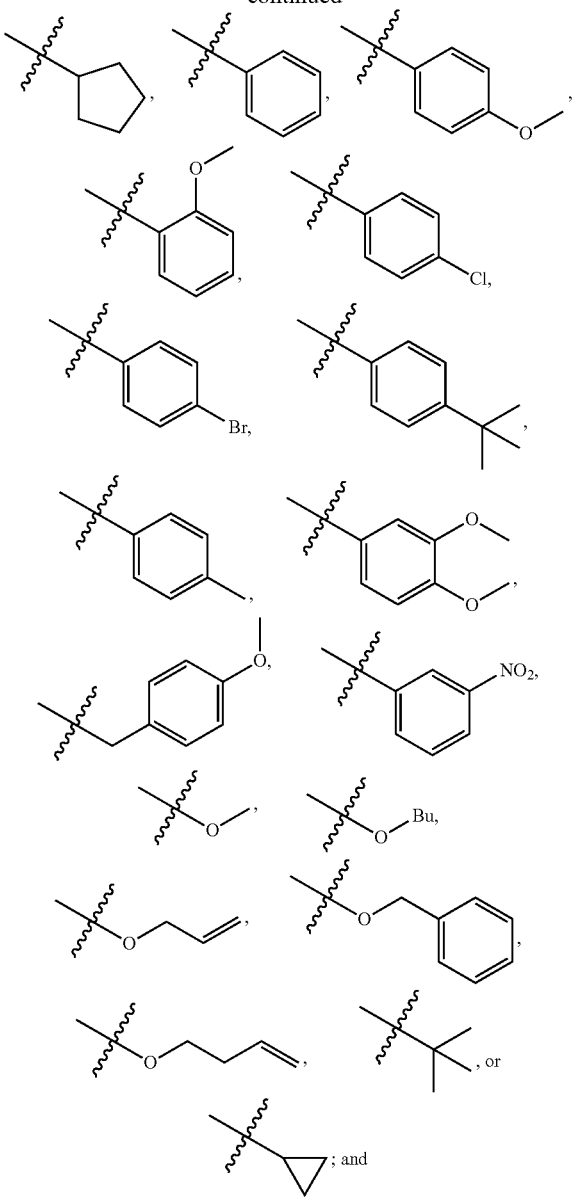
X represents O.
10. A molecule according to claim 5, wherein:
R¹ represents
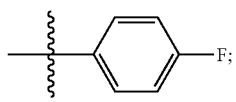
R² and R³ represent ethyl;
R⁴ represents H;
R⁵ represents
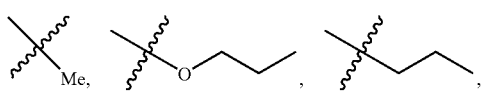
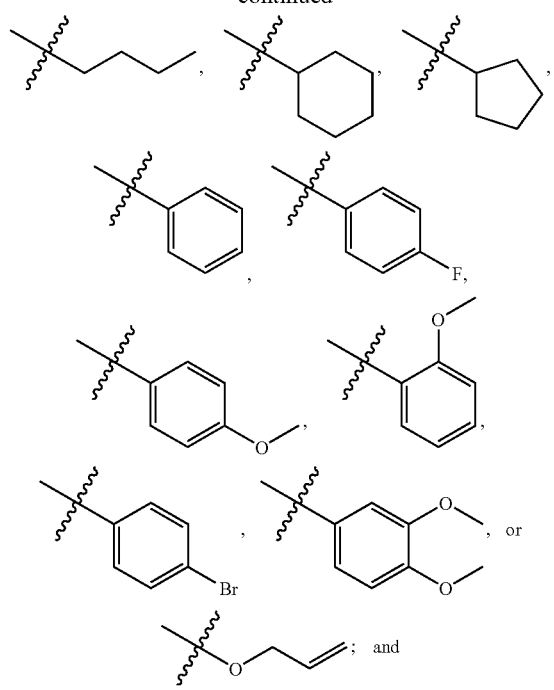
X represents O.
11. A molecule according to claim 5, wherein:
R¹ represents
R² and R³ represent ethyl;
R⁴ represents H;
R⁵ represents
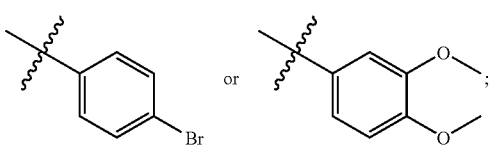
and
X represents O.
12. A molecule according to claim 5, wherein:
R¹ represents
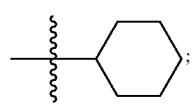
R² and R³ represent ethyl;
R⁴ represents H;

R⁵ represents

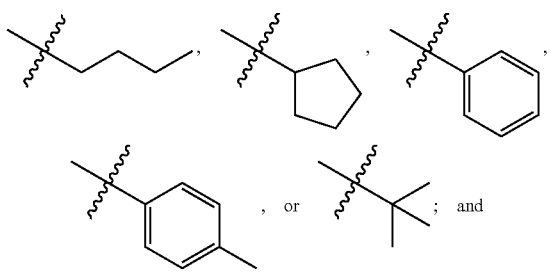

X represents O.

13. A molecule according to claim 1, wherein:
when R² represents H, R³ is not methyl.

14. A method of treating a patient infected with *Mycobacterium tuberculosis*, the method comprising administering to the patient a compound of formula I

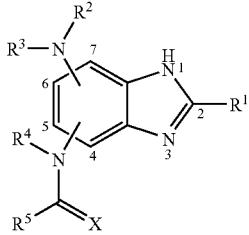

wherein:
R¹ represents $NH_2$, $NHR^6$, $NR^9R^{10}$, $NR^6CONR^9R^{10}$, $NR^6CSNR^9R^{10}$, OH, $OR^6$, SH, $SR^6$, CHO, $COOR^6$, $COR^6$, $CH_2OH$, $CR^7R^8OH$, $CH_2OR^6$, $CR^7R^8OR^6$, $CH_2NH_2$, $CR^7R^8NH_2$, $CR^7R^8NR^9R^{10}$, alkyl, cycloalkyl, aryl, or halo;
R² and R⁴ independently represent H, alkyl, cycloalkyl, or aryl;
R³ represents alkyl, cycloalkyl, or aryl;
R⁵ represents H, R⁶, $OR^6$, $SR^6$, $NH_2$, $NHR^6$, or $NR^9R^{10}$;
X represents O, S, NH, or $NR^6$;
R⁶, R⁷, R⁸, R⁹, and R¹⁰ independently represent alkyl, cycloalkyl, aryl, or halo; or
R² and R³; R⁴ and R⁵; and R⁹ and R¹⁰ independently, may be combined to represent a heterocyclic alkyl or heterocyclic aryl; or
R⁷ and R⁸ may be combined to represent a cycloalkyl;
alkyl groups are branched or unbranched, saturated or unsaturated, and have 1-18 carbon atoms in their longest chain;
cycloalkyl groups are carbocyclic or heterocyclic, fused or unfused, non-aromatic ring systems having a total of 5-16 ring members including substituent rings;
aryl groups are carbocyclic or heterocyclic;
carbocyclic aryl groups are fused or unfused ring systems having a total of 6-16 ring members including substituent rings;
heterocyclic aryl groups are fused or unfused ring systems having a total of 5-16 ring members including substituent rings;
halo substituents are fluoro, chloro, or bromo;
each alkyl, cycloalkyl, and aryl, independently, may be unsubstituted or substituted with one or more substituent at any position;
alkyl substituents are halo, hydroxyl, $OR^6$, $SR^6$, $NH_2$, $NHR^6$, $NR^9R^{10}$, cycloalkyl, or aryl;
cycloalkyl substituents are halo, hydroxyl, $OR^6$, $SR^6$, $NH_2$, $NHR^6$, $NR^9R^{10}$, alkyl, cycloalkyl, or aryl;
aryl substituents are halo, hydroxyl, $OR^6$, $SR^6$, $NH_2$, $NHR^6$, $NR^9R^{10}$, alkyl, cycloalkyl, aryl, nitro, or carboxyl; and
heterocyclic alkyl and heterocyclic aryl have at least one heteroatom selected from oxygen, nitrogen and sulfur; or
a pharmaceutically acceptable salt thereof.

15. A method of treating a patient infected with *Francisella tulerensis*, the method comprising administering to the patient a compound of formula I

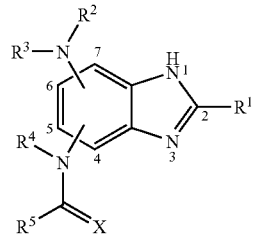

wherein:
R¹ represents $NH_2$, $NHR^6$, $NR^9R^{10}$, $NR^6CONR^9R^{10}$, $NR^6CSNR^9R^{10}$, OH, $OR^6$, SH, $SR^6$, CHO, $COOR^6$, $COR^6$, $CH_2OH$, $CR^7R^8OH$, $CH_2OR^6$, $CR^7R^8OR^6$, $CH_2NH_2$, $CR^7R^8NH_2$, $CR^7R^8NR^9R^{10}$, alkyl, cycloalkyl, aryl, or halo;
R² and R⁴ independently represent H, alkyl, cycloalkyl, or aryl;
R³ represents alkyl, cycloalkyl, or aryl;
R⁵ represents H, R⁶, $OR^6$, $SR^6$, $NH_2$, $NHR^6$, or $NR^9R^{10}$;
X represents O, S, NH, or $NR^6$;
R⁶, R⁷, R⁸, R⁹, and R¹⁰ independently represent alkyl, cycloalkyl, aryl, or halo; or
R² and R³; R⁴ and R⁵; and R⁹ and R¹⁰ independently, may be combined to represent a heterocyclic alkyl or heterocyclic aryl; or
R⁷ and R⁸ may be combined to represent a cycloalkyl;
alkyl groups are branched or unbranched, saturated or unsaturated, and have 1-18 carbon atoms in their longest chain;
cycloalkyl groups are carbocyclic or heterocyclic, fused or unfused, non-aromatic ring systems having a total of 5-16 ring members including substituent rings;
aryl groups are carbocyclic or heterocyclic;
carbocyclic aryl groups are fused or unfused ring systems having a total of 6-16 ring members including substituent rings;
heterocyclic aryl groups are fused or unfused ring systems having a total of 5-16 ring members including substituent rings;
halo substituents are fluoro, chloro, or bromo;
each alkyl, cycloalkyl, and aryl, independently, may be unsubstituted or substituted with one or more substituent at any position;
alkyl substituents are halo, hydroxyl, $OR^6$, $SR^6$, $NH_2$, $NHR^6$, $NR^9R^{10}$, cycloalkyl, or aryl;
cycloalkyl substituents are halo, hydroxyl, $OR^6$, $SR^6$, $NH_2$, $NHR^6$, $NR^9R^{10}$, alkyl, cycloalkyl, or aryl;

aryl substituents are halo, hydroxyl, $OR^6$, $SR^6$, $NH_2$, $NHR^6$, $NR^9R^{10}$, alkyl, cycloalkyl, aryl, nitro, or carboxyl; and heterocyclic alkyl and heterocyclic aryl have at least one heteroatom selected from oxygen, nitrogen and sulfur; or a pharmaceutically acceptable salt thereof.

16. A molecule according to claim 1, wherein:
$R^6$, $R^7$, $R^8$, $R^9$, and $R^{10}$ independently represent alkyl, cycloalkyl, or aryl.

17. A molecule according to claim 1, wherein:
$R^6$, $R^7$, $R^8$, $R^9$, and $R^{10}$ independently represent alkyl or aryl.

18. A method according to claim 14, wherein:
$R^6$, $R^7$, $R^8$, $R^9$, and $R^{10}$ independently represent alkyl, cycloalkyl, or aryl.

19. A method according to claim 15, wherein:
$R^6$, $R^7$, $R^8$, $R^9$, and $R^{10}$ independently represent alkyl, cycloalkyl, or aryl.

20. A molecule of formula I

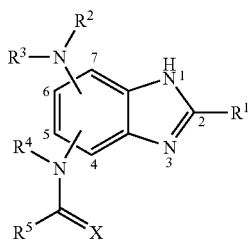

wherein:
$R^1$ represents $NH_2$, $NHR^6$, $NR^9R^{10}$, $NR^6CONR^9R^{10}$, $NR^6CSNR^9R^{10}$, OH, $OR^6$, SH, $SR^6$, CHO, $COOR^6$, $COR^6$, $CH_2OH$, $CR^7R^8OH$, $CH_2OR^6$, $CR^7R^8OR^6$, $CH_2NH_2$, $CR^7R^8NH_2$, $CR^7R^8NR^9R^{10}$, alkyl, cycloalkyl, aryl, or halo;

$R^2$ and $R^4$ independently represent H, alkyl, cycloalkyl, or aryl;

$R^3$ represents alkyl, cycloalkyl, aryl, CO(cycloalkyl), or CO(aryl);

$R^5$ represents H, $R^6$, $OR^6$, $SR^6$, $NH_2$, $NHR^6$, or $NR^9R^{10}$;

X represents O;

$R^6$, $R^7$, $R^8$, $R^9$, and $R^{10}$ independently represent alkyl, cycloalkyl, or aryl; or $R^2$ and $R^3$; $R^4$ and $R^5$; and $R^9$ and $R^{10}$ independently, may be combined to represent a heterocyclic alkyl or heterocyclic aryl; or $R^7$ and $R^8$ may be combined to represent a cycloalkyl;

alkyl groups are branched or unbranched, saturated or unsaturated, and have 1-18 carbon atoms in their longest chain;

cycloalkyl groups are carbocyclic or heterocyclic, fused or unfused, non-aromatic ring systems having a total of 5-16 ring members including substituent rings;

aryl groups are carbocyclic or heterocyclic;

carbocyclic aryl groups are fused or unfused ring systems having a total of 6-16 ring members including substituent rings;

heterocyclic aryl groups are fused or unfused ring systems having a total of 5-16 ring members including substituent rings;

halo substituents are fluoro, chloro, or bromo;

each alkyl, cycloalkyl, and aryl, independently, may be unsubstituted or substituted with one or more substituent at any position;

alkyl substituents are halo, hydroxyl, $OR^6$, $SR^6$, $NH_2$, $NHR^6$, $NR^9R^{10}$, cycloalkyl, or aryl;

cycloalkyl substituents are halo, hydroxyl, $OR^6$, $SR^6$, $NH_2$, $NHR^6$, $NR^9R^{10}$, alkyl, cycloalkyl, or aryl;

aryl substituents are halo, hydroxyl, $OR^6$, $SR^6$, $NH_2$, $NHR^6$, $NR^9R^{10}$, alkyl, cycloalkyl, aryl, nitro, or carboxyl; and heterocyclic alkyl and heterocyclic aryl have at least one heteroatom selected from oxygen, nitrogen and sulfur; or a pharmaceutically acceptable salt thereof.

21. A method of treating a patient infected with *Mycobacterium tuberculosis*, the method comprising administering to the patient a compound of formula I

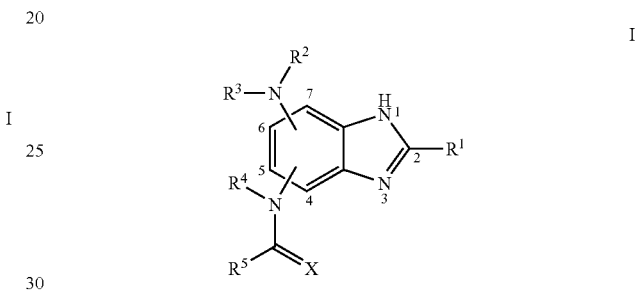

wherein:
$R^1$ represents $NH_2$, $NHR^6$, $NR^9R^{10}$, $NR^6CONR^9R^{10}$, $NR^6CSNR^9R^{10}$, OH, $OR^6$, SH, $SR^6$, CHO, $COOR^6$, $COR^6$, $CH_2OH$, $CR^7R^8OH$, $CH_2OR^6$, $CR^7R^8OR^6$, $CH_2NH_2$, $CR^7R^8NH_2$, $CR^7R^8NR^9R^{10}$, alkyl, cycloalkyl, aryl, or halo;

$R^2$ and $R^4$ independently represent H, alkyl, cycloalkyl, or aryl;

$R^3$ represents alkyl, cycloalkyl, aryl, or $COR^6$;

$R^5$ represents H, $R^6$, $OR^6$, $SR^6$, $NH_2$, $NHR^6$, or $NR^9R^{10}$;

X represents O, S, NH, or $NR^6$;

$R^6$, $R^7$, $R^8$, $R^9$, and $R^{10}$ independently represent alkyl, cycloalkyl, or aryl; or $R^2$ and $R^3$; $R^4$ and $R^5$; and $R^9$ and $R^{10}$ independently, may be combined to represent a heterocyclic alkyl or heterocyclic aryl; or $R^7$ and $R^8$ may be combined to represent a cycloalkyl;

alkyl groups are branched or unbranched, saturated or unsaturated, and have 1-18 carbon atoms in their longest chain;

cycloalkyl groups are carbocyclic or heterocyclic, fused or unfused, non-aromatic ring systems having a total of 5-16 ring members including substituent rings;

aryl groups are carbocyclic or heterocyclic;

carbocyclic aryl groups are fused or unfused ring systems having a total of 6-16 ring members including substituent rings;

heterocyclic aryl groups are fused or unfused ring systems having a total of 5-16 ring members including substituent rings;

halo substituents are fluoro, chloro, or bromo;

each alkyl, cycloalkyl, and aryl, independently, may be unsubstituted or substituted with one or more substituent at any position;

alkyl substituents are halo, hydroxyl, $OR^6$, $SR^6$, $NH_2$, $NHR^6$, $NR^9R^{10}$, cycloalkyl, or aryl;

cycloalkyl substituents are halo, hydroxyl, $OR^6$, $SR^6$, $NH_2$, $NHR^6$, $NR^9R^{10}$, alkyl, cycloalkyl, or aryl;

aryl substituents are halo, hydroxyl, $OR^6$, $SR^6$, $NH_2$, $NHR^6$, $NR^9R^{10}$, alkyl, cycloalkyl, aryl, nitro, or carboxyl; and heterocyclic alkyl and heterocyclic aryl have at least one heteroatom selected from oxygen, nitrogen and sulfur; or a pharmaceutically acceptable salt thereof.

22. A method of treating a patient infected with *Francisella tulerensis*, the method comprising administering to the patient a compound of formula I

I wherein:
$R^1$ represents $NH_2$, $NHR^6$, $NR^9R^{10}$, $NR^6CONR^9R^{10}$, $NR^6CSNR^9R^{10}$, OH, $OR^6$, SH, $SR^6$, CHO, $COOR^6$, $COR^6$, $CH_2OH$, $CR^7R^8OH$, $CH_2OR^6$, $CR^7R^8OR^6$, $CH_2NH_2$, $CR^7R^8NH_2$, $CR^7R^8NR^9R^{10}$, alkyl, cycloalkyl, aryl, or halo;

$R^2$ and $R^4$ independently represent H, alkyl, cycloalkyl, or aryl;

$R^3$ represents alkyl, cycloalkyl, aryl, or $COR^6$;

$R^5$ represents H, $R^6$, $OR^6$, $SR^6$, $NH_2$, $NHR^6$, or $NR^9R^{10}$;

X represents O, S, NH, or $NR^6$;

$R^6$, $R^7$, $R^8$, $R^9$, and $R^{10}$ independently represent alkyl, cycloalkyl, or aryl; or $R^2$ and $R^3$; $R^4$ and $R^5$; and $R^9$ and $R^{10}$ independently, may be combined to represent a heterocyclic alkyl or heterocyclic aryl; or $R^7$ and $R^8$ may be combined to represent a cycloalkyl;

alkyl groups are branched or unbranched, saturated or unsaturated, and have 1-18 carbon atoms in their longest chain;

cycloalkyl groups are carbocyclic or heterocyclic, fused or unfused, non-aromatic ring systems having a total of 5-16 ring members including substituent rings;

aryl groups are carbocyclic or heterocyclic;

carbocyclic aryl groups are fused or unfused ring systems having a total of 6-16 ring members including substituent rings;

heterocyclic aryl groups are fused or unfused ring systems having a total of 5-16 ring members including substituent rings;

halo substituents are fluoro, chloro, or bromo;

each alkyl, cycloalkyl, and aryl, independently, may be unsubstituted or substituted with one or more substituent at any position;

alkyl substituents are halo, hydroxyl, $OR^6$, $SR^6$, $NH_2$, $NHR^6$, $NR^9R^{10}$, cycloalkyl, or aryl;

cycloalkyl substituents are halo, hydroxyl, $OR^6$, $SR^6$, $NH_2$, $NHR^6$, $NR^9R^{10}$, alkyl, cycloalkyl, or aryl;

aryl substituents are halo, hydroxyl, $OR^6$, $SR^6$, $NH_2$, $NHR^6$, $NR^9R^{10}$, alkyl, cycloalkyl, aryl, nitro, or carboxyl; and heterocyclic alkyl and heterocyclic aryl have at least one heteroatom selected from oxygen, nitrogen and sulfur; or a pharmaceutically acceptable salt thereof.

23. A molecule of formula I

I wherein:
$R^1$ represents $R^2$ and $R^3$ represent ethyl;

$R^4$ represents H;

$R^5$ represents

-continued

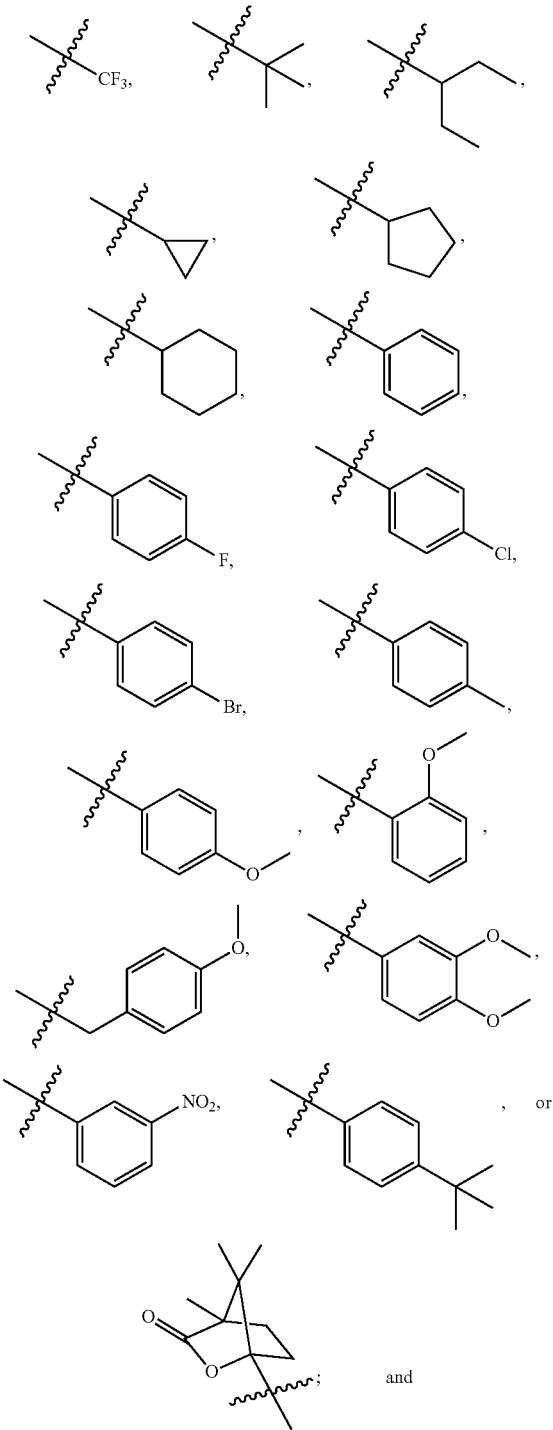

X represents O.

24. A molecule of formula I

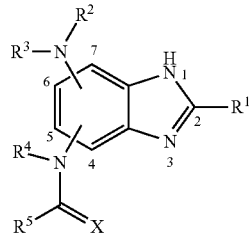

wherein:
$R^1$ represents $NH_2$, $NHR^6$, $NR^9R^{10}$, $NR^6CONR^9R^{10}$, $NR^6CSNR^9R^{10}$, OH, $OR^6$, SH, $SR^6$, CHO, $COOR^6$, $COR^6$, $CH_2OH$, $CR^7R^8OH$, $CH_2OR^6$, $CR^7R^8OR^6$, $CH_2NH_2$, $CR^7R^8NH_2$, $CR^7R^8NR^9R^{10}$, alkyl, cycloalkyl, aryl, or halo;

$R^2$ and $R^4$ independently represent H, alkyl, cycloalkyl, or aryl;

$R^3$ represents alkyl, cycloalkyl, aryl, or $COR^6$;

$R^5$ represents H, $R^6$, $OR^6$, $SR^6$, $NH_2$, $NHR^6$, or $NR^9R^{10}$;

X represents S, NH, or $NR^6$;

$R^6$, $R^7$, $R^8$, $R^9$, and $R^{10}$ independently represent alkyl, cycloalkyl, or aryl; or $R^2$ and $R^3$; $R^4$ and $R^5$; and $R^9$ and $R^{10}$ independently, may be combined to represent a heterocyclic alkyl or heterocyclic aryl; or $R^7$ and $R^8$ may be combined to represent a cycloalkyl;

alkyl groups are branched or unbranched, saturated or unsaturated, and have 1-18 carbon atoms in their longest chain;

cycloalkyl groups are carbocyclic or heterocyclic, fused or unfused, non-aromatic ring systems having a total of 5-16 ring members including substituent rings;

aryl groups are carbocyclic or heterocyclic;

carbocyclic aryl groups are fused or unfused ring systems having a total of 6-16 ring members including substituent rings;

heterocyclic aryl groups are fused or unfused ring systems having a total of 5-16 ring members including substituent rings;

halo substituents are fluoro, chloro, or bromo;

each alkyl, cycloalkyl, and aryl, independently, may be unsubstituted or substituted with one or more substituent at any position;

alkyl substituents are halo, hydroxyl, $OR^6$, $SR^6$, $NH_2$, $NHR^6$, $NR^9R^{10}$, cycloalkyl, or aryl;

cycloalkyl substituents are halo, hydroxyl, $OR^6$, $SR^6$, $NH_2$, $NHR^6$, $NR^9R^{10}$, alkyl, cycloalkyl, or aryl;

aryl substituents are halo, hydroxyl, $OR^6$, $SR^6$, $NH_2$, $NHR^6$, $NR^9R^{10}$, alkyl, cycloalkyl, aryl, nitro, or carboxyl; and heterocyclic alkyl and heterocyclic aryl have at least one heteroatom selected from oxygen, nitrogen and sulfur; or a pharmaceutically acceptable salt thereof.

* * * * *